(12) United States Patent
Zwirn et al.

(10) Patent No.: US 8,062,223 B2
(45) Date of Patent: Nov. 22, 2011

(54) USING PULSED-WAVE ULTRASONOGRAPHY FOR DETERMINING AN ALIASING-FREE RADIAL VELOCITY SPECTRUM OF MATTER MOVING IN A REGION

(75) Inventors: Gil Zwirn, Petach-Tikva (IL); Solange Akselrod, Givat Shmuel (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 919 days.

(21) Appl. No.: 11/795,918

(22) PCT Filed: Jan. 25, 2006

(86) PCT No.: PCT/IL2006/000105
§ 371 (c)(1),
(2), (4) Date: Feb. 29, 2008

(87) PCT Pub. No.: WO2006/080011
PCT Pub. Date: Aug. 3, 2006

(65) Prior Publication Data
US 2008/0210016 A1   Sep. 4, 2008

Related U.S. Application Data

(60) Provisional application No. 60/646,510, filed on Jan. 25, 2005.

(51) Int. Cl.
*A61B 8/00* (2006.01)
(52) U.S. Cl. ........ 600/437; 600/453; 600/454; 600/455; 600/456; 600/457
(58) Field of Classification Search ................... 600/437, 600/453–457
See application file for complete search history.

(56) References Cited

U.S. PATENT DOCUMENTS
5,027,122 A   6/1991   Wieler
2004/0102706 A1   5/2004   Christopher et al.

FOREIGN PATENT DOCUMENTS
WO   WO 2005/065028   7/2005

OTHER PUBLICATIONS
International Preliminary Report on Patentability Dated Aug. 9, 2007 From the International Bureau of WIPO Re.: Application No. PCT/IL2006/000105.

*Primary Examiner* — Tse Chen
*Assistant Examiner* — Baisakhi Roy

(57) ABSTRACT

Using pulsed-wave (PW) ultrasonography for determining an aliasing-free radial velocity spectrum of matter moving in a region. Includes: transmitting into the region a plurality of pulse trains of sound waves at two or more different pulse repetition frequencies; spectrally analyzing each pulse train, for evaluating a Doppler frequency spectrum associated with each pulse train; combining frequency components of Doppler frequency spectrum of each pulse train, for obtaining aliasing-free instantaneous Doppler frequency spectrum for the region; using Doppler effect for translating aliasing-free frequency spectrum to aliasing-free radial velocity spectrum. Implementable using pulsed-wave Doppler (PWD), color flow Doppler (CFD), tissue Doppler imaging (TDI), or pulsed-wave (PW) ultrasonography. Applicable to liquid or/and solid forms of matter, moving in a two- or three-dimensional region. Matter is any substance or material, composed of organics or/and inorganics, which is part of a non-living object, or, part of a human or animal subject.

26 Claims, 12 Drawing Sheets

US 8,062,223 B2

USING PULSED-WAVE ULTRASONOGRAPHY FOR DETERMINING AN ALIASING-FREE RADIAL VELOCITY SPECTRUM OF MATTER MOVING IN A REGION

RELATED APPLICATIONS

This Application is a National Phase of PCT Patent Application No. PCT/IL2006/000105 having International Filing Date of Jan. 25, 2006, which claims the benefit of U.S. Provisional Patent Application No. 60/646,510 filed on Jan. 25, 2005. The contents of the above Applications are all incorporated herein by reference.

FIELD AND BACKGROUND OF THE INVENTION

The present invention relates to ultrasonography, and more particularly, to a method of using pulsed-wave (PW) ultrasonography for determining an aliasing-free radial velocity spectrum of matter moving in a region. The present invention also relates to a method of using pulsed-wave (PW) ultrasonography for performing an ultrasound or medical imaging procedure on a subject.

The present invention is implementable by using any of the three main types or modalities, i.e., pulsed-wave Doppler (PWD), color flow Doppler (CFD), or tissue Doppler imaging (TDI), of pulsed-wave (PW) ultrasonography, which are used for measuring and determining radial velocity spectra of matter moving in a region. The present invention is applicable for determining an aliasing-free radial velocity spectrum of different forms, e.g., liquid or/and solid forms, of matter, moving in a (two-dimensional areal or three-dimensional volumetric) region. Such matter moving in the region is generally any substance or material, composed of organic or/and inorganic species, being of liquid or/and solid form, which is part of a non-living object, or, part of a human or animal subject. The present invention is implementable in a wide variety of different applications that are practiced in a wide variety of different fields, such as ultrasonography, medical imaging, acoustics, seismology, sonar imaging, radar technology, electronic warfare, lidar (light detection and ranging). An important exemplary application of the present invention in the fields of ultrasonography and medical imaging is echocardiography. The present invention is commercially applicable by being readily integratable and implementable with currently used pulsed-wave (PW) ultrasonography equipment and hardware (devices, apparatuses, systems).

Ultrasonography (i.e., use of ultrasound waves), pulsed-wave (PW) ultrasonography and the main modalities (i.e., pulsed-wave Doppler (PWD), color flow Doppler (CFD), and tissue Doppler imaging (TDI)), thereof, used for measuring and determining radial velocity spectra of matter moving in a region, aliasing, the theory, principles, and practices thereof, and, related and associated applications and subjects thereof, are well known and taught about in the prior art, and currently widely practiced. For the purpose of establishing the scope, meaning, and fields of application, of the present invention, following are selected definitions and exemplary usages of terminology used for disclosing the present invention.

Matter Moving in a Region

Herein, the term 'matter' generally refers to any substance or material which occupies space. In general, the substance or material is composed of organic species, or/and inorganic species. The matter (substance or material) can be of different forms, for example, liquid or/and solid. Moreover, the matter (substance or material) can be part of a non-living object, or, part of a human or animal subject. Herein, the term 'region' generally refers to any, usually continuous, segment of a surface or of a (two-dimensional or three-dimensional) space (or area). Moreover, the region can be part of a wet (i.e., liquid) or dry (i.e., gaseous (e.g., air)) environment. Accordingly, herein, the phrase 'matter moving in a region' generally refers to any substance or material, composed of organic or/and inorganic species, and being of liquid or/and solid form, which occupies a segment of a surface or of a (two-dimensional or three-dimensional) space (or area) that is part of a wet or dry environment.

In the fields of ultrasonography and medical imaging, particularly relevant exemplary types of matter moving in a region are blood, or tissue (e.g., muscle tissue), moving in an organ (e.g., heart, uterus, kidney, pancreas) or in some other region in the body of a (adult or fetal) human or animal subject. In the field of seismology, particularly relevant exemplary types of matter moving in a region are lava, ground water, or petroleum, moving within ground beneath the earth's surface. In the field of sonar imaging, particularly relevant exemplary types of matter moving in a region are marine vessels (e.g., submersible undersea marine vessels or craft), or marine animals (e.g., fish, whales, manatee), moving beneath the surface of (ocean or fresh) water. In the field of radar technology, particularly relevant exemplary types of matter moving in a region are vehicles (e.g., cars, trucks), marine craft (e.g., ships, boats, buoys), aircraft (e.g., airplanes, helicopters, blimps, drones, rockets, missiles), or a space craft. In the field of electronic warfare, particularly relevant exemplary types of matter moving in a region are military (land, air, marine) vehicle or craft. In the field of lidar (light detection and ranging), particularly relevant exemplary types of matter moving in a region are ground based small sized ('hard-to-detect') landscape objects or features (e.g., power transmission lines, rocks, roadways).

Pulsed-Wave (PW) Ultrasonography and Three Modalities Thereof.

Currently, there exist three main modalities (i.e., pulsed-wave Doppler (PWD), color flow Doppler (CFD), and tissue Doppler imaging (TDI)), of pulsed-wave (PW) ultrasonography which are used for measuring and determining radial velocity spectra of matter moving in a region, each of which is briefly defined and described hereinbelow.

Pulsed Wave Doppler (PWD) Modality

Consistent with prior art teachings [e.g., 1], herein, the pulsed wave Doppler (PWD) modality of pulsed-wave (PW) ultrasonography refers to a technique which provides information regarding the spectrum of radial velocities (i.e., the velocity component along the line-of-sight between the transducer and the region of interest) for a selected depth along a specific angular direction, as a function of time. The data is displayed as a two-dimensional graph, where the abscissa is the radial velocity (which may either be positive or negative) and the ordinate is the discrete time index. The gray level of each pixel denotes the ratio (for the scanned volume of at least part of the region) between the number of the components or elements (e.g., particles) of the matter moving at the relevant radial velocity and the total number of components or elements (particles). Thus, the outlines of the graph show the maximal velocity as a function of time. For example, in echocardiography, PWD studies are commonly used for measuring and determining radial velocity spectra of various different types and forms of matter or objects (e.g., blood, muscle tissue, valves, blood clots) moving in a cardiac muscle type of region of a subject. Two well known important applications of this technique are the evaluation of forward mitral flow (especially associated with the condition of mitral stenosis in a human subject), and the measurement of blood flow in the descending aorta (for assessing the amount of aortic regurgitation).

Color Flow Doppler (CFD) Modality

Consistent with prior art teachings [e.g., 1, 2], herein, the color flow Doppler (CFD) modality of pulsed-wave (PW) ultrasonography refers to a technique which superimposes a color representation of the mean radial velocity (for each pixel) over the two-dimensional (or three-dimensional) ultrasonic image of the matter (e.g., blood, tissue) moving in a region. The generally accepted color coding displays matter flowing towards the transducer as red and yellow hues, and matter flowing away from the transducer as blue and aqua. A well known important application of this technique is the evaluation of mitral valve regurgitation.

Tissue Doppler Imaging (TDI) Modality

Consistent with prior art teachings [e.g., 3], herein, the tissue Doppler imaging (TDI) modality of pulsed-wave (PW) ultrasonography refers to a technique which evaluates radial tissue motion in vascular and cardiac imaging. As for the CFD modality, in the TDI modality, velocity information is superimposed over a B-Scan two-dimensional image. In most relevant applications, knowing the precise temporal variability in the local signal is crucial for clinical diagnosis, so that the frame-rates used in the TDI modality are usually very high (e.g., in many cases, on the order of one hundred frames per second or more).

Brief Theoretical Basis of the Three Modalities (PWD, CFD, TDI)

All three modalities utilize the standard pulsed-wave (PW) scheme. For the pulsed wave Doppler (PWD) modality, a pulse train is transmitted in a specific direction, and the returned signal is sampled at a time slice corresponding to the relevant range. For the color flow Doppler (CFD) and tissue Doppler imaging (TDI) modalities, pulse trains are transmitted in different directions, spanning the imaging plane (or imaging volume), and the returned signal for each pulse is measured at constant time intervals, corresponding to equally spaced ranges (commonly referred to as 'range-gates'). The radial velocity measurements are based on the Doppler effect, which (for ultrasonic imaging) are described [e.g., 2] in terms of the Doppler frequency or Doppler shift, defined by equation (1):

$$f_D = \frac{2fv\cos(\theta)}{c} \quad (1)$$

where $f$ is the transmitted frequency; $v$ is the absolute flow velocity; $\theta$ is the angle between the effective directions of the ultrasonic beam and the flow velocity; $c$ is the wave speed; and $f_D$ is the Doppler frequency or Doppler shift, corresponding to the difference between the frequencies of the observed and transmitted ultrasound waves. The radial velocity component is $v \cos(\theta)$, therefore, the Doppler shift is directly proportional to the radial velocity of the matter moving in the region.

For each small region of interest (again, for the PWD modality there is only one), a single sample is collected for each pulse in the pulse train. Thus, the sampling interval $\Delta$ is the inverse of the pulse repetition frequency (PRF), $f_p$. A straightforward method for estimating the Doppler shift is by applying Fast Fourier Transform (FFT) to the measurements (after subtracting the baseline of the frequency used for transmission). The ratio (for the relevant volume) between the number of the components or elements (e.g., particles) of the matter moving with each Doppler shift, and the total number of components or elements (particles) is simply described by the power spectrum (i.e., the element-by-element square of the FFT of the signal). For FFT, the frequency resolution, $\delta f_D$, of the output is defined [e.g., 4] by equation (2):

$$\delta f_D = \frac{1}{N\Delta} \quad (2)$$

where N is the number of pulses in the pulse train. The corresponding radial velocity measurement resolution, $\delta v_r$, is defined by equation (3):

$$\delta v_r = \frac{c \cdot \delta f_D}{2f} = \frac{c}{2fN\Delta}. \quad (3)$$

This method is applicable to the PWD modality, where a single region of interest is used, and hence the information for the entire relevant volume is collected in $N\Delta$. In this configuration, N is usually 64, 128, or 256.

In the CFD modality, however, both high spatial resolution and relatively high frame rates are obtained by using very low values (e.g., 3-8) of N. The local flow velocity is coarsely approximated [e.g., 2] based on calculating the signal correlation (for each range gate in each beam position) between consecutive pulses in the train.

The configuration used in the TDI modality is somewhat more complex. For example, the wall motion of the cardiac muscle is about 10 times slower than the flow velocity of blood cells (the wall motion ranges from 0 to 0.24 m/s [e.g., 5]). Adequate frequency resolution for small N values, which are imperative for obtaining acceptable temporal and spatial resolution, requires using relatively low PRFs. This, in turn, reduces either the spatial or the temporal resolution of the collected data. In order to support the high frame rates necessary for the TDI modality, only a small number of beam positions are scanned at each frame (about 16). The radial velocity is estimated using either short FFTs or correlation techniques.

Aliasing Associated with Pulsed-Wave (PW) Ultrasonography, and Problems Thereof.

All three imaging modalities, PWD, CFD, and TDI, of pulsed-wave (PW) ultrasonography suffer from the same major limitation: aliasing. Consistent with prior art teachings [e.g., 4], herein, the term aliasing refers to an artifactual type of phenomenon that arises when the Nyquist critical frequency is exceeded by at least one frequency component of the input signal.

For any sampling interval $\Delta$ (corresponding to a PRF $f_p = \Delta^{-1}$), there is also a special frequency $f_c$, called the Nyquist critical frequency, defined [e.g., 4] by equation (4):

$$f_c = \frac{1}{2\Delta} \quad (4)$$

When sampling a signal, that is not bandwidth limited to the range between the negative Nyquist critical frequency and the positive Nyquist critical frequency, $[-f_c, f_c]$, any frequency component outside these limits is falsely translated, or aliased, into that range, by the very act of discrete sampling. Note that, unlike the frequency resolution (equation (2)), the Nyquist frequency is independent of the length of the pulse train N.

Furthermore, particularly applicable to pulsed-wave (PW) ultrasonography, is that the Nyquist frequency is inversely proportional to the maximal penetration depth R, defined by equation (5):

$$R = \frac{c\Delta}{2} \quad (5)$$

It is assumed that each pulse is transmitted only after reception of reflections from the furthest relevant range of the previous pulse.

In the field of radar technology, when there exists the possibility for aliasing to occur during Doppler measurements, the Doppler measurements are considered as being ambiguous, i.e., characterized by ambiguities.

Prior Art Techniques for Addressing Aliasing, and Limitations Thereof.

Until now, several techniques for bypassing, overcoming, or reducing (suppressing), the undesirable effects of aliasing have been suggested. Fundamental methods of such techniques [e.g., 6, 7, 8] are particularly applicable to the CFD modality of pulsed-wave (PW) ultrasonography, and are based on tracking the mean Doppler frequencies immediately before and immediately after the Nyquist frequency, either along the temporal axis or along the spatial axis. Such techniques are limited by being relatively noise-sensitive (i.e., strong noise may cause false alarms in the identification of aliased signals), and may only double the maximal unambiguous frequency (i.e., the maximal 'true' frequency at which aliasing is absent).

There is a technique [9] which is applicable to the PWD modality of pulsed-wave (PW) ultrasonography, that enables measurement of frequencies exceeding the Nyquist frequency, so long as the total bandwidth of the measured signal is less than, or equal to, the pulse repetition frequency (PRF). This technique simply varies interpretation of the measured spectral pattern, by moving the center Doppler frequency of the analyzed band from zero to the instantaneous mean Doppler frequency, thereby avoiding the aliasing effect on the displayed signal.

A more complex technique exists [10] which is designed for suppressing aliasing during PWD imaging. This technique involves summing the signal along skewed lines in the time range plane (that is, prior to applying FFT), where the slope is chosen to follow the movement of the reflectors or scatterers along the ultrasonic beam for each velocity in the velocity spectrum. Only when the slope matches the actual velocity do the received echoes match in phase and amplitude, giving a peak in the spectrum at the actual velocity value. This concept is implemented by performing integration over the two-dimensional power spectrum of the time range signal, weighted by a velocity dependent spectral window function.

The double repetition-rate technique, which enables the estimation of Doppler spectra (for the PWD modality) with a bandwidth higher than the pulse repetition frequency (PRF), was first introduced by Newhouse et al. [11]. This technique is based on the observation that the measured Doppler frequency for aliased signals depends on the transmitted PRF, whereas the measured Doppler frequency for true, non-aliased signals, is independent of the PRF. Thus, if a system uses two alternating PRFs, then, comparing the two spectra taken at the two PRFs enables identification of aliased frequency components, i.e., the aliased frequency components are displaced relative to zero frequency in accordance with the PRF, while the non-aliased spectral components are not displaced.

A main limitation of the double repetition-rate technique is that the maximal unambiguous frequency (i.e., the maximal 'true' frequency at which aliasing is absent) is, at best, increased by a factor of 2. Additionally, this technique is only applicable when the Doppler frequency peaks are relatively narrow and easily discernable (resolvable) from each other. However, it is well known [e.g., 11] in clinical practice that many high velocity flows, such as during mitral stenosis, are turbulent, and thus generate Doppler spectra characterized by relatively broad and non-discernable (non-resolvable) peaks.

Another technique [12] which is particularly applicable to the PWD modality of pulsed-wave (PW) ultrasonography utilizes two ultrasound carrier frequencies, such that an appropriate processing of the measured Doppler frequencies results in an extended range of mean velocity measurement of matter moving in a region. As understood from equation (1), the carrier frequency also affects the Doppler shift, so that the outcome of using two different carrier frequencies is similar to that of using two pulse repetition frequency PRFs. With the extended mean velocity information, the complex Doppler signal is interpolated to reconstruct the aliased Doppler spectra. Such a technique is useful, however, it is also limited in that interpolation inherently introduces inaccurate information into the imaging system. These inaccuracies become severe when the data region includes several dominant velocities, whereas the interpolation scheme assumes a specific mean frequency. This is the case in the presence of several simultaneous jets within the region of interest, for example, due to a combination of mitral valve regurgitation and a shunt between the left ventricle and the right ventricle.

In radar technology, there are teachings [e.g., 13] of a basic technique for bypassing, overcoming, or reducing (suppressing), undesirable effects of Doppler measurement ambiguities (analogous to occurrence of aliasing in pulsed-wave (PW) ultrasonography). The technique is based on transmitting pulses at two alternating pulse repetition frequencies (PRFs), and leads to evaluating the dominant Doppler frequency corresponding to a very narrow velocity spectrum corresponding to an airborne target. Historically, this technique has never been suggested, thought, or considered, as being applicable to addressing the problem of aliasing in pulsed-wave (PW) ultrasonography. This technique is analogous to bypassing, overcoming, or reducing (suppressing), the undesirable effects of aliasing in the color flow Doppler (CFD) and tissue Doppler imaging (TDI) modalities of pulsed-wave (PW) ultrasonography.

Accordingly, based on the preceding discussion, prior art techniques for addressing aliasing which occurs when using pulsed-wave (PW) ultrasonography for determining radial velocity spectra of matter moving in a region are significantly limited.

There is thus a need for, and it would be highly advantageous to have a method of using pulsed-wave (PW) ultrasonography for determining an aliasing-free radial velocity spectrum of matter moving in a region. There is also a need for, and it would be highly advantageous to have a method of using pulsed-wave (PW) ultrasonography for performing an ultrasound or medical imaging procedure on a subject.

There is also a need for such an invention which is implementable by using any of the three main types or modalities, i.e., pulsed-wave Doppler (PWD), color flow Doppler (CFD), or tissue Doppler imaging (TDI), of pulsed-wave (PW) ultrasonography, which are used for measuring and determining radial velocity spectra of matter moving in a region.

There is also a need for such an invention which is applicable for determining an aliasing-free radial velocity spectrum of different forms, e.g., liquid or/and solid forms, of matter, moving in a (two-dimensional areal or three-dimensional volumetric) region, where such matter moving in the region is generally any substance or material, composed of organic or/and inorganic species, being of liquid or/and solid form, which is part of a non-living object, or, part of a human or animal subject. Moreover, there is need for such an invention which is implementable in a wide variety of different applications that are practiced in a wide variety of different fields, such as ultrasonography, medical imaging, acoustics, seismology, sonar imaging, radar technology, electronic warfare, lidar (light detection and ranging). Furthermore, there is a need for such an invention which is commercially applicable by being readily integratable and implementable with currently used pulsed-wave (PW) ultrasonography equipment and hardware (devices, apparatus, systems).

SUMMARY OF THE INVENTION

The present invention relates to a method of using pulsed-wave (PW) ultrasonography for determining an aliasing-free radial velocity spectrum of matter moving in a region. The present invention also relates to a method of using pulsed-wave (PW) ultrasonography for performing an ultrasound or medical imaging procedure on a subject.

The present invention is implementable by using any of the three main types or modalities, i.e., pulsed-wave Doppler (PWD), color flow Doppler (CFD), or tissue Doppler imaging (TDI), of pulsed-wave (PW) ultrasonography, which are used for measuring and determining radial velocity spectra of matter moving in a region. The present invention is applicable for determining an aliasing-free radial velocity spectrum of different forms, e.g., liquid or/and solid forms, of matter, moving in a (two-dimensional areal or three-dimensional volumetric) region. Such matter moving in the region is generally any substance or material, composed of organic or/and inorganic species, being of liquid or/and solid form, which is part of a non-living object, or, part of a human or animal subject.

The present invention is implementable in a wide variety of different applications that are practiced in a wide variety of different fields, such as ultrasonography, medical imaging, acoustics, seismology, sonar imaging, radar technology, electronic warfare, lidar (light detection and ranging). An important exemplary application of the present invention in the fields of ultrasonography and medical imaging is echocardiography. The present invention is commercially applicable by being readily integratable and implementable with currently used pulsed-wave (PW) ultrasonography equipment and hardware (devices, apparatus, systems).

Thus, according to the present invention, there is provided a method of using pulsed-wave ultrasonography for determining an aliasing-free radial velocity spectrum of matter moving in a region, the method comprising: (a) transmitting into the region a plurality of pulse trains of sound waves at two or more different pulse repetition frequencies; (b) spectrally analyzing each pulse train, for evaluating a Doppler frequency spectrum associated with each pulse train; (c) combining frequency components of the Doppler frequency spectrum of each pulse train, for obtaining an aliasing-free instantaneous Doppler frequency spectrum for the region; and (d) using the Doppler effect for translating the aliasing-free frequency spectrum to the aliasing-free radial velocity spectrum of the matter moving in the region.

According to another aspect of the present invention, there is provided a method of using pulsed-wave ultrasonography for performing an ultrasound or medical imaging procedure on a subject, the method comprising: (a) transmitting into a region of the subject a plurality of pulse trains of sound waves at two or more different pulse repetition frequencies; (b) spectrally analyzing each pulse train, for evaluating a Doppler frequency spectrum associated with each pulse train; (c) combining frequency components of the Doppler frequency spectrum of each pulse train, for obtaining an aliasing-free instantaneous Doppler frequency spectrum for the region of the subject; and (d) using the Doppler effect for translating the aliasing-free frequency spectrum to the aliasing-free radial velocity spectrum of the matter moving in the region.

According to further characteristics in preferred embodiments of the invention described below, in step (a), the plurality of pulse trains of sound waves are alternately or simultaneously transmitted into the region at the two or more different pulse repetition frequencies.

According to further characteristics in preferred embodiments of the invention described below, the simultaneous transmission involves use of a different phase coding or/and a different carrier frequency of the sound waves, for each pulse repetition frequency.

According to further characteristics in preferred embodiments of the invention described below, step (b) includes applying at least one spectral analysis technique selected from the group consisting of Discrete Fourier Transform (DFT), Fast Fourier Transform (FFT), signal correlation, Burg method, and Minimum Variance Method (MVM).

According to further characteristics in preferred embodiments of the invention described below, in step (c) the frequency components correspond to a plurality of frequencies in a range between negative Nyquist critical frequency and positive Nyquist critical frequency, as measured at one of the pulse repetition frequencies, being a sum of several frequency components.

According to further characteristics in preferred embodiments of the invention described below, step (c) includes imposing a specific assumption regarding the aliasing-free instantaneous Doppler frequency spectrum for the region.

According to further characteristics in preferred embodiments of the invention described below, the pulsed-wave ultrasonography is of a modality selected from the group consisting of color flow Doppler (CFD), tissue Doppler imaging (TDI), and pulsed-wave Doppler (PWD).

According to further characteristics in preferred embodiments of the invention described below, the pulsed-wave ultrasonography is of a modality selected from the group consisting of color flow Doppler (CFD) and tissue Doppler imaging (TDI).

According to further characteristics in preferred embodiments of the invention described below, the pulsed-wave ultrasonography is of a color flow Doppler (CFD) modality.

According to further characteristics in preferred embodiments of the invention described below, the pulsed-wave ultrasonography is of a tissue Doppler imaging (TDI) modality.

According to further characteristics in preferred embodiments of the invention described below, the pulsed-wave ultrasonography is of a pulsed-wave Doppler (PWD) modality.

According to further characteristics in preferred embodiments of the invention described below, only a single dominant Doppler frequency in the aliasing-free Doppler frequency spectrum is estimated, by separately measuring the dominant Doppler frequency at each pulse repetition frequency.

According to further characteristics in preferred embodiments of the invention described below, the estimation is performed by utilizing a set of linear equations, wherein each linear equation describes a group of possible aliasing-free Doppler frequencies matching the measured dominant Doppler frequency, for each pulse train.

According to further characteristics in preferred embodiments of the invention described below, the lowest Doppler frequency included in all groups of possible aliasing-free frequencies is considered the dominant Doppler frequency in the aliasing-free Doppler frequency spectrum.

According to further characteristics in preferred embodiments of the invention described below, step (c) includes solving a series of recursive equations, wherein each recursive equation describes dependence of the frequency components of the Doppler frequency spectrum of each pulse train on the aliasing-free instantaneous Doppler frequency spectrum for the region.

According to further characteristics in preferred embodiments of the invention described below, the pulse repetition frequencies and a number of pulses in each pulse train are determined, for obtaining a same frequency resolution of each Doppler frequency spectrum associated with each pulse train.

According to further characteristics in preferred embodiments of the invention described below, an initial condition for solving the series of recursive equations is where maximal non-zero Doppler frequency component of the aliasing-free instantaneous Doppler frequency spectrum is known a priori.

According to further characteristics in preferred embodiments of the invention described below, an analog low-pass filter is applied to signals returned for each pulse train, and an initial condition for solving the series of recursive equations is where maximal non-zero Doppler frequency component of the aliasing-free instantaneous Doppler frequency spectrum is a pre-determined constant matching a transfer function of to the low-pass filter.

According to further characteristics in preferred embodiments of the invention described below, the matter is a substance or material composed of organic species or/and inorganic species.

According to further characteristics in preferred embodiments of the invention described below, the matter is of a liquid form or/and of a solid form.

According to further characteristics in preferred embodiments of the invention described below, the matter is part of a non-living object, or part of a human or animal subject.

According to further characteristics in preferred embodiments of the invention described below, the matter is blood or tissue.

According to further characteristics in preferred embodiments of the invention described below, the blood or tissue is moving in an organ in a body of a human or animal subject.

According to further characteristics in preferred embodiments of the invention described below, the organ is a heart, a uterus, a kidney, or a pancreas.

According to further characteristics in preferred embodiments of the invention described below, the matter is lava, ground water, or petroleum.

According to further characteristics in preferred embodiments of the invention described below, the matter is a marine vessel, or a marine animal.

According to further characteristics in preferred embodiments of the invention described below, the matter is a vehicle, a marine craft, an aircraft, or a space craft.

According to further characteristics in preferred embodiments of the invention described below, the matter is a ground based small sized landscape object or feature.

According to further characteristics in preferred embodiments of the invention described below, the object or feature is a power transmission line, a rock, or a roadway.

According to further characteristics in preferred embodiments of the invention described below, the region is segment of a surface, or a segment of a two-dimensional or three-dimensional space.

According to further characteristics in preferred embodiments of the invention described below, the region is part of a wet or dry environment.

According to further characteristics in preferred embodiments of the invention described below, used in a type of procedure selected from the group consisting of ultrasonography, medical imaging, acoustics, seismology, sonar imaging, radar technology, electronic warfare, and lidar (light detection and ranging).

According to further characteristics in preferred embodiments of the invention described below, the type of the ultrasonography or medical imaging is echocardiography.

The present invention is implemented by performing procedures, steps, and sub-steps, in a manner selected from the group consisting of manually, semi-automatically, fully automatically, and a combination thereof, involving use and operation of system units, system sub-units, devices, assemblies, sub-assemblies, mechanisms, structures, components, and elements, and, peripheral equipment, utilities, accessories, and materials, in a manner selected from the group consisting of manually, semi-automatically, fully automatically, and a combination thereof. Moreover, according to actual procedures, steps, sub-steps, system units, system sub-units, devices, assemblies, sub-assemblies, mechanisms, structures, components, and elements, and, peripheral equipment, utilities, accessories, and materials, used for implementing a particular embodiment of the disclosed invention, the procedures, steps, and sub-steps, are performed by using hardware, software, or/and an integrated combination thereof, and the system units, sub-units, devices, assemblies, sub-assemblies, mechanisms, structures, components, and elements, and, peripheral equipment, utilities, accessories, and materials, operate by using hardware, software, or/and an integrated combination thereof.

In particular, software used for implementing the present invention includes operatively connected and functioning written or printed data, in the form of software programs, software routines, software sub-routines, software symbolic languages, software code, software instructions or protocols, software algorithms, or/and a combination thereof. In particular, hardware used for implementing the present invention includes operatively connected and functioning electrical, electronic or/and electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or/and combinations thereof, involving digital or/and analog operations. Accordingly, the present invention is implemented by using an integrated combination of the just described software and hardware.

BRIEF DESCRIPTION OF THE DRAWINGS

The present invention is herein described, by way of example only, with reference to the accompanying drawings.

With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

Figure 1:
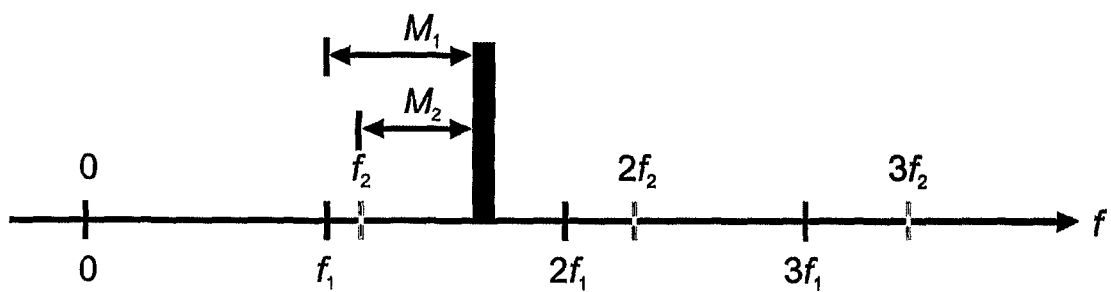
FIG. 1 is a schematic diagram illustrating an exemplary aliasing effect occurring when sampling a single frequency signal using two different PRFs, $f_1$ and $f_2$, wherein the frequency measured using $f_1$ is $M_1$, and the frequency measured using $f_2$ is $M_2$; where the actual frequency (marked by the bold long vertical line) is higher than both $M_1$ and $M_2$ in accordance with the relation: $f_a=(f_1+=(f_2+M_2)$.

The present invention relates to a method of using pulsed-wave (PW) ultrasonography for determining an aliasing-free radial velocity spectrum of matter moving in a region. The present invention also relates to a method of using pulsed-wave (PW) ultrasonography for performing an ultrasound or medical imaging procedure on a subject.

The present invention is implementable by using any of the three main types or modalities, i.e., pulsed-wave Doppler (PWD), color flow Doppler (CFD), or tissue Doppler imaging (TDI), of pulsed-wave (PW) ultrasonography, which are used for measuring and determining radial velocity spectra of matter moving in a region. The present invention is applicable for determining an aliasing-free radial velocity spectrum of different forms, e.g., liquid or/and solid forms, of matter, moving in a (two-dimensional areal or three-dimensional volumetric) region. Such matter moving in the region is generally any substance or material, composed of organic or/and inorganic species, being of liquid or/and solid form, which is part of a non-living object, or, part of a human or animal subject.

The present invention is implementable in a wide variety of different applications that are practiced in a wide variety of different fields, such as ultrasonography, medical imaging, acoustics, seismology, sonar imaging, radar technology, electronic warfare, lidar (light detection and ranging). An important exemplary application of the present invention in the fields of ultrasonography and medical imaging is echocardiography. The present invention is commercially applicable by being readily integratable and implementable with currently used pulsed-wave (PW) ultrasonography equipment and hardware (devices, apparatus, systems).

The generalized method of using pulsed-wave ultrasonography for determining an aliasing-free radial velocity spectrum of matter moving in a region, of the present invention, includes the following main steps: (a) transmitting into the region a plurality of pulse trains of sound waves at two or more different pulse repetition frequencies; (b) spectrally analyzing each pulse train, for evaluating a Doppler frequency spectrum associated with each pulse train; (c) combining frequency components of the Doppler frequency spectrum of each pulse train, for obtaining an aliasing-free instantaneous Doppler frequency spectrum for the region; and (d) using the Doppler effect for translating the aliasing-free frequency spectrum to the aliasing-free radial velocity spectrum of the matter moving in the region.

The method of using pulsed-wave ultrasonography for performing an ultrasound or medical imaging procedure on a subject, includes the following main steps: (a) transmitting into a region of the subject a plurality of pulse trains of sound waves at two or more different pulse repetition frequencies; (b) spectrally analyzing each pulse train, for evaluating a Doppler frequency spectrum associated with each pulse train; (c) combining frequency components of the Doppler frequency spectrum of each pulse train, for obtaining an aliasing-free instantaneous Doppler frequency spectrum for the region of the subject; and (d) using the Doppler effect for translating the aliasing-free frequency spectrum to the aliasing-free radial velocity spectrum of the matter moving in the region.

A main aspect of novelty and inventiveness of the present invention is that the method provides for evaluating the dominant Doppler frequency in the color flow Doppler (CFD) modality or the tissue Doppler imaging (TDI) modality of pulsed-wave (PW) ultrasonography in the presence of aliasing.

Another main aspect of novelty and inventiveness of the present invention is that the method provides for accurately and precisely quantitatively evaluating the Doppler frequency spectrum in the pulsed-wave Doppler (PWD) modality of pulsed-wave (PW) ultrasonography in the presence of aliasing.

It is to be understood that the present invention is not limited in its application to the details of the order or sequence, and number, of procedures, steps, and sub-steps, of operation or implementation of the method set forth in the following illustrative description, accompanying drawings, and examples, unless otherwise specifically stated herein. The present invention is capable of other embodiments and of being practiced or carried out in various ways. Although procedures, steps, and sub-steps, which are equivalent or similar to those illustratively described herein can be used for practicing or testing the present invention, suitable procedures, steps, and sub-steps, are illustratively described and exemplified herein.

It is also to be understood that all technical and scientific words, terms, or/and phrases, used herein throughout the present disclosure have either the identical or similar meaning as commonly understood by one of ordinary skill in the art to which this invention belongs, unless otherwise specifically defined or stated herein. Phraseology, terminology, and, notation, employed herein throughout the present disclosure are for the purpose of description and should not be regarded as limiting.

Moreover, all technical and scientific words, terms, or/and phrases, introduced, defined, described, or/and exemplified, in the above Background section, are equally or similarly applicable in the illustrative description of the preferred embodiments, examples, and appended claims, of the present invention.

Procedures, steps, sub-steps, equipment, and materials, as well as operation and implementation, of exemplary preferred embodiments, alternative preferred embodiments, specific configurations, and, additional and optional aspects, characteristics, or features, thereof, of the method of using pulsed-wave (PW) ultrasonography for determining an aliasing-free radial velocity spectrum of matter moving in a region, and of the method of using pulsed-wave ultrasonography for performing an ultrasound or medical imaging procedure on a subject, according to the present invention, are better understood with reference to the following illustrative description and accompanying drawings. Throughout the following illustrative description and accompanying drawings, same reference numbers, or/and letters, refer to same components. Additionally, throughout the following illustrative description and accompanying drawings, superscripts are 'exclusively' used as indices, and not for raising the indicated (superscripted) function or parameter to a power.

In the following illustrative description of the method of the present invention, included are main or principal procedures, steps, and sub-steps, needed for sufficiently understanding proper 'enabling' utilization and implementation of the disclosed method. Accordingly, description of various possible preliminary, intermediate, minor, or/and optional, procedures, steps, or/and sub-steps, of secondary importance with respect to enabling implementation of the invention, which are readily known by one of ordinary skill in the art, or/and which are available in the relevant prior art and technical literature are at most only briefly indicated herein.

In the following illustrative description of the present invention, there is first provided illustrative description of an exemplary preferred embodiment of the generalized method of using pulsed-wave (PW) ultrasonography for determining an aliasing-free radial velocity spectrum of matter moving in a region, followed thereafter by detailed illustrative description of two exemplary specific preferred embodiments of the generalized method. The first exemplary specific preferred embodiment of the generalized method is particularly applicable to, and implementable by using, the color flow Doppler (CFD) modality or the tissue Doppler imaging (TDI) modality of pulsed-wave (PW) ultrasonography. The second exemplary specific preferred embodiment of the generalized method is particularly applicable to, and implementable by using, the pulsed-wave Doppler (PWD) modality of pulsed-wave (PW) ultrasonography. Thereafter is provided illustrative description of an exemplary preferred embodiment of the method of using pulsed-wave ultrasonography for performing an ultrasound or medical imaging procedure on a subject.

Thereafter, are provided two examples of the second exemplary specific preferred embodiment of the generalized method of using pulsed-wave (PW) ultrasonography for determining an aliasing-free radial velocity spectrum of matter moving in a region, as particularly applicable to, and implementable by using, the pulsed-wave Doppler (PWD) modality of pulsed-wave (PW) ultrasonography.

Generalized Method—Applicable to Color Flow Doppler (CFD), Tissue Doppler Imaging (TDI), or Pulsed-Wave Doppler (PWD), Modalities Thus, according to a main aspect of the present invention, there is provision of a method of using pulsed-wave ultrasonography for determining an aliasing-free radial velocity spectrum of matter moving in a region.

In Step (a) of the method of using pulsed-wave ultrasonography for determining an aliasing-free radial velocity spectrum of matter moving in a region, there is transmitting into the region a plurality of pulse trains of sound waves at two or more different pulse repetition frequencies.

For a given ultrasound system, Step (a) corresponds to defining the waveform of the signals transmitted into the region within which the matter moves. A standard requirement of performing Step (a) is that the overall period of time or duration of a set of pulse trains which are consecutively transmitted must be sufficiently small to ensure measurement of a single, approximately non-variable, actual (signal) Doppler frequency spectrum.

In general, in Step (a), the plurality of pulse trains of sound waves are alternately or simultaneously transmitted into the region at two or more different pulse repetition frequencies. Simultaneous transmission involves use of a different phase coding or/and a different carrier frequency of the sound waves, for each pulse repetition frequency.

In Step (b) of the method, there is spectrally analyzing each pulse train, for evaluating a Doppler frequency spectrum associated with each pulse train.

In general, Step (b) is performed by applying any of a wide variety of known spectral analysis techniques used for signal processing. For example, Step (b) is performed by applying at least one spectral analysis technique selected from the group consisting of Discrete Fourier Transform (DFT), Fast Fourier Transform (FFT), signal correlation, Burg method, and Minimum Variance Method (MVM).

The signal correlation technique is performed by correlating the measured signal of ultrasonic reflections of each pulse of each pulse train with the transmitted signal of each corresponding pulse of each corresponding pulse train. The Burg method or the Minimum Variance Method (MVM) are exemplary advanced spectral analysis techniques. Preferably, Step (b) is performed by using the above stated Fast Fourier Transform (FFT) technique, or the correlation technique.

In Step (c) of the method, there is combining frequency components of the Doppler frequency spectrum of each pulse train, for obtaining an aliasing-free instantaneous Doppler frequency spectrum for the region.

The combination of frequency components is derived from the fact, that the frequency components, corresponding to a plurality of single frequencies M in the range $[-f_c, f_c]$, as measured at one of the pulse repetition frequencies (PRFs), $f_p$, is actually the sum of the Doppler frequency components corresponding to the group of frequencies $f$, described by equation (6):

$$f = M + n f_p \quad |n = 0, \pm 1, \pm 2, \ldots \quad (6)$$

where $f_c$ is the Nyquist critical frequency, and $f_p$ is the Pulse Repetition Frequency (PRF). Equation (6) expresses the periodicity in the frequency plane [e.g., 4], forced by aliasing. The frequency components correspond to a plurality of frequencies in a range between the negative Nyquist critical frequency and the positive Nyquist critical frequency, as measured at one of the pulse repetition frequencies, being a sum of several frequency components. For example, a single period of the frequency plane is described by the frequency range $[-f_c, f_c]$, or by the frequency range $[0, 2f_c)$. As described by equation (4), $f_c = f_p/2$, so that the period in the frequency plane is $f_p$.

When a plurality of pulse trains of sound waves at two or more different (alternating or simultaneous) pulse repetition frequencies is used, the Doppler frequency spectrum measured at each pulse repetition frequency (PRF) provides partial information regarding the different Doppler frequency components of the actual (signal) Doppler spectrum. Determining the actual Doppler frequency spectrum requires imposing a specific assumption regarding the actual (signal) Doppler spectrum on above equation (6). Such an assumption may refer, for example, to the maximal non-zero Doppler frequency component in the actual (signal) Doppler spectrum, to the number of peaks within the actual (signal) Doppler spectrum, or to the width of each peak within the actual (signal) Doppler spectrum. Accordingly, Step (c) includes imposing a specific assumption regarding the aliasing-free instantaneous Doppler frequency spectrum for the region.

In Step (d) of the method, there is using the Doppler effect, described by equation (1), for translating the aliasing-free frequency spectrum to the aliasing-free radial velocity spectrum of the matter moving in the region.

The procedures illustratively described hereinbelow are particular cases which are applicable to the main modalities (i.e., pulsed-wave Doppler (PWD) and color flow Doppler (CFD), and, tissue Doppler imaging (TDI)), of pulsed-wave (PW) ultrasonography.

Applicability to the Color Flow Doppler (CFD) Modality, or to the Tissue Doppler Imaging (TDI) Modality When taking samples at a given PRF $f_p$, the signal measured at any frequency M in the range $[-f_c, f_c]$ is actually the sum of the signal at the following frequencies $f$.

$$f = M + nf_p \mid n = 0, \pm 1, \pm 2, \ldots \quad (6)$$

The preceding statement and equation (6) are clearly understood by noting the periodicity in the frequency plane, forced by aliasing. The frequency plane is characterized by the period being in the frequency range of either $[0, 2f_c]$ or $[-f_c, f_c]$, and since $f_c = f_p/2$ [equation (4)], the period in the frequency plane is simply $f_p$.

Accordingly, based on the hereinabove generalized method as applied to the color flow Doppler (CFD) modality or the tissue Doppler imaging (TDI) modality of pulsed-wave (PW) ultrasonography, only a single dominant Doppler frequency in the aliasing-free Doppler frequency spectrum is estimated. Such estimation is performed by separately measuring the dominant Doppler frequency at each of a number of, for example, two, pulse repetition frequencies.

The pulse trains should use two different PRFs, $f_1$ and $f_2$ ($f_2 > f_1$). The measured Doppler shifts, $M_1$ and $M_2$ respectively, correspond to the actual Doppler frequencies:

$$f = M_1 + n_1 f_1 \mid n_1 = 0, \pm 1, \pm 2, \quad (7)$$

and:

$$f = M_2 + n_2 f_2 \mid n_2 = 0, \pm 1, \pm 2, \ldots \quad (8)$$

Accordingly, the estimation is performed by utilizing a set of linear equations, wherein each linear equation describes a group of possible aliasing-free Doppler frequencies matching the measured dominant Doppler frequency, for each pulse train. The actual dominant Doppler frequency, $f_a$, must comply with both equations (7) and (8):

$$f_a = M_1 + n_1 f_1 = M_2 + n_2 f_2 \mid n_1, n_2 = 0, \pm 1, \pm 2, \ldots \quad (9)$$

The lowest Doppler frequency included in all of the groups of possible aliasing-free frequencies is considered the dominant Doppler frequency in the aliasing-free Doppler frequency spectrum. Thus, the best estimate for $f_a$ is the solution for which both $n_1$ and $n_2$ are minimal, as shown in FIG. 1, a schematic diagram illustrating an exemplary aliasing effect occurring when sampling a single frequency signal using two different PRFs, $f_1$ and $f_2$, wherein the frequency measured using $f_1$ is $M_1$, and the frequency measured using $f_2$ is $M_2$; where the actual frequency (marked by the bold long vertical line) is higher than both $M_1$ and $M_2$ in accordance with the relation: $f_a = (f_1 + M_1) = (f_2 + M_2)$.

The above procedure should lead to precise evaluation of the Doppler shift, and therefore, of the measured velocity. However, the number of pulses transmitted in each direction using the new procedure is twice that in standard configurations. The refresh rate is accordingly decreased by a factor of 2 (which may necessitate decreasing the scanned area or volume). In order to reduce this effect, one can assume that the value of $n_1$ (or $n_2$) remains constant for F consecutive frames, and use the dual-PRF scheme only once every F frames. The value of F should be adjusted for each scanned organ and specific application.

In order to determine the ratio between the effective unambiguous bandwidth of the dual-PRF configuration and the bandwidth corresponding to the higher PRF, $f_2$, one should simply count the number of possible different values of $M_1$ for any given $M_2$. For example, if $f_1$ is an integral multiple of $(f_2 - f_1)$, this ratio is simply $f_1/(f_2 - f_1)$. However, it should be emphasized, that the difference between $f_1$ and $f_2$ should be greater than (or equal to) the measurement accuracy $\Delta f$ (for each PRF separately). This is a condition for the changes (if any) in the frequency measurement, caused by changing the PRF, to be measurable. Thus, generally speaking, a good approximation for the maximal effective bandwidth, which is attainable by the dual-PRF scheme, is: $f_2 \cdot \lfloor f_1 / \Delta f \rfloor$.

Applicability to the Pulsed-Wave Doppler (PWD) Modality
Basic Concept

In the case of PWD, each pulse train is used for estimating the current wideband spectrum of the Doppler shifts. Assuming N samples (pulses) are used, the FFT output is a complex array of length N, whose n'th frequency index corresponds to the frequency $f^n$:

$$f^n = \frac{n}{N} f_p = \frac{n}{N\Delta} \quad \mid n = 0, 1, \ldots, N-1 \quad (10)$$

This result can be derived directly from equations (2) and (4).

If the actual spectrum of the signal is frequency bound to the range $[0, 2f_c]$, the value of the n'th measured element, $M^n$, is equal to the actual signal at the corresponding frequency, $S^n$:

$$M^n = S^n \mid n = 0, 1, \ldots, N-1 \quad (11)$$

On the other hand, aliasing occurs when the actual spectrum of the signal is frequency bound to the range $[0, f_{max})$, and $f_{max}$ is greater than $f_p$. Assuming that $\alpha \cdot f_p \leq f_{max} < (\alpha + 1) \cdot f_p$, where $\alpha$ is a positive integral denoted the "maximal fold index", one obtains equation (12):

$$M^n = \sum_{k=0}^{\alpha} S^{n+kN} \quad \mid n = 0, 1, \ldots, N-1 \quad (12)$$

where $S^n$ is the actual frequency component at the frequency:

$$f^n = \frac{n}{N} f_p = \frac{n}{N\Delta} \quad \mid n = 0, 1, \ldots, (\alpha+1) \cdot N - 1 \quad (13)$$

(here n can be greater than N−1).

Thus, based on the hereinabove generalized method as applied to the pulsed-wave Doppler (PWD) modality of pulsed-wave (PW) ultrasonography, overcoming the undesirable effects of aliasing is accomplished by solving a series of recursive equations, wherein each recursive equation describes dependence of the frequency components of the Doppler frequency spectrum of each pulse train on the aliasing-free instantaneous Doppler frequency spectrum for the region.

Note that $f_{max}$ may be forced by applying an analog low-pass filter to the returned signal, prior to sampling. The cut-off frequency of the low-pass filter should be set so as to assure that the filter's gain at frequencies exceeding $f_{max}$ should be negligible (the signal attenuation at the higher frequency components, caused by the filter's roll-off, may be corrected-for at post-processing, since the filter's frequency response is predetermined).

A main goal is to estimate the actual signal spectrum, $S^n$, based on the measurements, $M^n$. For the sake of simplicity, the derivation is performed for $\alpha=1$, but an analogous technique can be applied to higher values of $\alpha$. As in the case of CFD and TDI, preferably, two PRFs are used, denoted $f_1$ and $f_2$ (the number of PRFs should be set to $\alpha+1$). Each pulse train shall include $N_1$ pulses transmitted at $f_1$, followed by $N_2$ pulses transmitted at $f_2$. The spectra measured using $f_1$ and $f_2$ are denoted $M_1^n$ and $M_2^n$, respectively. In this case, the signal spectrum cannot be calculated using standard FFT, which requires using arrays whose length is an integral power of 2. Discrete Fourier Transform (DFT) is used instead.

This exemplary specific preferred embodiment of the generalized method includes determining the pulse repetition frequencies and a number of pulses in each pulse train, for obtaining a same frequency resolution for each Doppler frequency spectrum associated with each pulse train. For example, a same frequency resolution of two PRFs are denoted $\delta f_1$ and $\delta f_2$, as indicated in equation (14):

$$\delta f_1 = \delta f_2 = \delta f \tag{14}$$

The number of pulses transmitted at each PRF is denoted $N_1$ and $N_2$, and the PRFs themselves are $f_1$ and $f_2$. Use of equations (2) and (4) readily leads to the possible solution defined by equations (15) and (16):

$$N_2 = N_1 + 1 \tag{15}$$

$$\frac{f_1}{N_1} = \frac{f_2}{N_2} \Rightarrow f_2 = \frac{N_2}{N_1} f_1 = \frac{N_1 + 1}{N_1} f_1 \tag{16}$$

For $\alpha=1$, an optimal setting (relating to the number of pulses transmitted) is achieved when $f_1$ is half the value of $f_{max}$. Using N to denote the number of pulses per train, required to obtain the same frequency resolution in an aliasing-free configuration (using the PRF $f_{max}$), where N is an even number, one obtains equation (17):

$$N_1 = \frac{N}{2} \text{ and } N_2 = \frac{N}{2} + 1 \tag{17}$$

$$f_2 = \frac{N+2}{N} f_1 \tag{18}$$

In this case, the total number of pulses in the new train is only N+1, which is very close to the number of pulses in the aliasing-free configuration.

In the current configuration ($\alpha=1$), equation (12) yields:

$$M_1^n = S^n + S^{n+\frac{N}{2}} \quad | n = 0, 1, \ldots, \frac{N}{2} - 1 \tag{19}$$

$$M_2^n = S^n + S^{n+(\frac{N}{2}+1)} \quad | n = 0, 1, \ldots, \frac{N}{2}$$

However, since the maximal non-zero frequency component in the actual signal is at $f_{max}$, whereas $f_{max} = 2f_1$, and $f_2$ is somewhat greater than $f_1$:

$$S^{(\frac{N}{2}-1)+(\frac{N}{2}+1)} = S^{(\frac{N}{2})+(\frac{N}{2}+1)} = 0 \tag{20}$$

and therefore:

$$M_2^{\frac{N}{2}-1} = S^{\frac{N}{2}-1} \tag{21}$$

$$M_2^{\frac{N}{2}} = S^{\frac{N}{2}}$$

From equations (20) and (21), an initial condition for solving the series of recursive equations is where the maximal non-zero Doppler frequency component of the aliasing-free instantaneous Doppler frequency spectrum is known a priori.

Alternatively, as stated hereinabove, an analog low-pass filter can be applied to signals returned for each pulse train, and an initial condition for solving the series of recursive equations is where the maximal non-zero Doppler frequency component of the aliasing-free instantaneous Doppler frequency spectrum is a pre-determined constant matching a transfer function of the low-pass filter.

Figure 2:
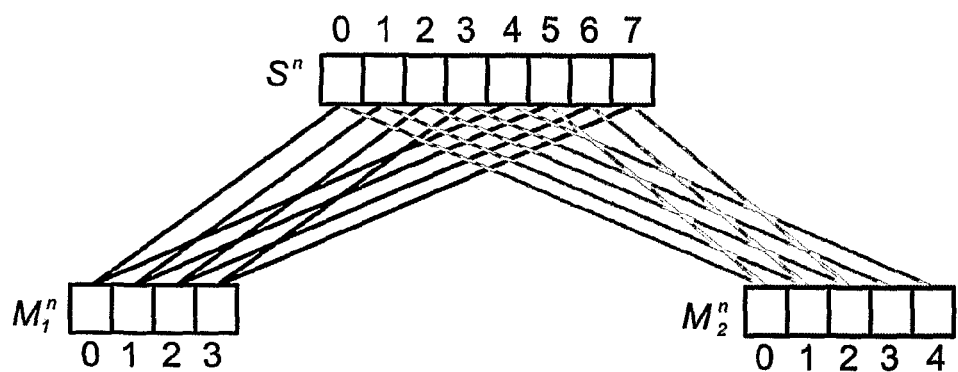
FIG. 2 is a schematic diagram illustrating the mapping of each actual frequency component, $S''$, to the signal spectra measured by using two different (alternating or simultaneous) pulse repetition frequencies (PRFs), $M_1''$ and $M_2''$, for N=8, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

The preceding formulation is illustrated for N=8 in FIG. 2, a schematic diagram illustrating the mapping of each actual frequency component, $S^n$, to the signal spectra measured by using two different (alternating or simultaneous) pulse repetition frequencies (PRFs), $M_1^n$ and $M_2^n$, for N=8, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

Thus, equation (19) can be rewritten in recursive form:

$$S^n = \begin{cases} M_1^n - S^{n+\frac{N}{2}} & n = 0, 1, \ldots, \frac{N}{2} - 2 \\ M^{n-(\frac{N}{2}+1)} - S^{n-(\frac{N}{2}+1)} & n = \frac{N}{2} + 1, \ldots, N - 1 \end{cases} \tag{22}$$

using the initial condition in equation (21), restated as:

$$S^{\frac{N}{2}-1} = M_2^{\frac{N}{2}-1} \tag{23}$$

$$S^{\frac{N}{2}} = M_2^{\frac{N}{2}}$$

Equation (22) can be reformatted to iterative form, which is more efficient for programming:

$$\text{for } n = 0 \text{ to } \left(\frac{N}{2} - 2\right) \tag{24}$$

$$S^n = M_1^n - S^{n+\frac{N}{2}}$$

$$S^{n+(\frac{N}{2}+1)} = M_2^n - S^n$$

In order to clarify equations (23) and (24), the procedure for the example of N=8 is enclosed:

$$S^3 = M_2^3$$

$$S^4 = M_2^4$$

$$S^0 = M_1^0 - S^4 \quad S^5 = M_2^0 - S^0$$

$$S^1 = M_1^1 - S^5 \quad S^6 = M_2^1 - S^1$$

$$S^2 = M_1^2 - S^6 \quad S^7 = M_2^2 - S^2 \tag{25}$$

This solution utilizes only one initial condition for the iterative calculation of the rest of the spectrum: the condition regarding $S^{N/2}$ ($S^4$ in the example). A second solution can be given, using the initial condition for $S^{(N/2)-1}$ ($S^3$ in the example), so that equation (24) can be replaced by:

$$\text{for } n = \left(\frac{N}{2} - 2\right) \text{ to } 1 \text{ step } -1 \tag{26}$$

$$S^{n+\left(\frac{N}{2}+1\right)} = M_1^{n+1} - S^{n+1}$$

$$S^n = M_2^n - S^{n+\left(\frac{N}{2}+1\right)}$$

which yields, for N=8:

$$S^3 = M_2^3$$

$$S^4 = M_2^4$$

$$S^7 = M_1^3 - S^3 \quad S^2 = M_2^2 - S^7$$

$$S^6 = M_1^2 - S^2 \quad S^1 = M_2^1 - S^6$$

$$S^5 = M_1^1 - S^1 \quad S^0 = M_2^0 - S^5 \tag{27}$$

Performance Evaluation

Theoretically, the aforementioned procedure should produce an accurate estimate of the entire actual spectrum, $S^n$. However, as explained below, the calculated spectrum is noise sensitive. The noise (for each frequency) is assumed to be additive and complex. Each component of the noise (real and imaginary) is Normally distributed, with a 0 mean and a standard deviation σ. It is assumed that each component of each frequency is independent of the others.

For two random variables X and Y, the definitions of variance (Var) and covariance (Cov) yield:

$$\text{Var}(X+Y) = \text{Var}(X) + \text{Var}(Y) + 2\text{Cov}(X,Y)$$

$$\text{Var}(X-Y) = \text{Var}(X) + \text{Var}(Y) - 2\text{Cov}(X,Y) \tag{28}$$

If X and Y are independent, we obtain:

$$\text{Var}(X+Y) = \text{Var}(X-Y) = \text{Var}(X) + \text{Var}(Y) \tag{29}$$

Therefore, when adding or subtracting A independent elements with equal variance, the variance of the result is A times greater than that of each element, and the standard deviation is $\sqrt{A}$ times higher than the standard deviation per element.

Figure 3A:
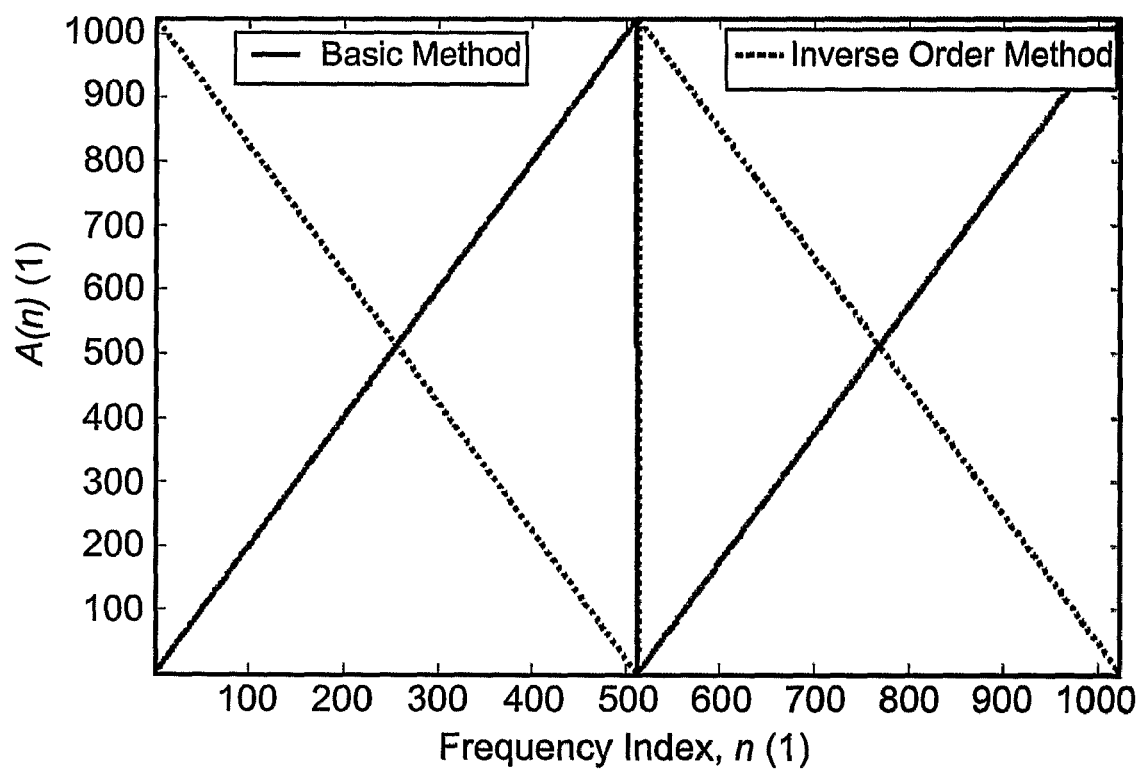
FIG. 3a is a graphical diagram illustrating the number of elements added (or subtracted) during calculation of the actual (signal) Doppler spectrum for each frequency index, A(n), for N=1024, using the Basic method (solid line) and the Inverse method (dashed line), where, for each method, the function is in the shape of a triangular wave, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

In our case, the estimated value for the n'th frequency index is the result of adding or subtracting A(n) values. For the first solution, A(n) is in the form of a triangular wave, as shown in FIG. 3a, below, being a graphical diagram illustrating the number of elements added (or subtracted) during calculation of the actual (signal) Doppler spectrum for each frequency index, A(n), for N=1024, using the Basic method (solid line) and the Inverse method (dashed line), where, for each method, the function is in the shape of a triangular wave, as applied in the pulsed-wave Doppler (PWD) modality of pulsed-wave (PW) ultrasonography:

$$A(n) = \begin{cases} 2n+2 & n = 0, 1, \ldots, \frac{N}{2} - 2 \\ 1 & n = \frac{N}{2} - 1, \frac{N}{2} \\ 2n - N + 1 & n = \frac{N}{2} + 1, \ldots, N-1 \end{cases} \tag{30}$$

For the second solution, A(n) is very similar, but almost flipped from left to right (FIG. 3a):

$$A(n) = \begin{cases} N - 2n - 1 & n = 0, 1, \ldots, \frac{N}{2} - 2 \\ 1 & n = \frac{N}{2} - 1, \frac{N}{2} \\ 2N - 2n & n = \frac{N}{2} + 1, \ldots, N-1 \end{cases} \tag{31}$$

For each component of each frequency index, the standard deviation is simply $\sqrt{A(n)} \cdot \sigma$. The maximal value of A(n) is (N−1), and therefore we expect the ratio between the maximal absolute error in the reconstructed spectrum $S^n$ and the mean absolute error in the samples σ to be approximately $\sqrt{N-1}$. Thus, for N=64, this ratio should roughly be 7.94.

Figure 3B:
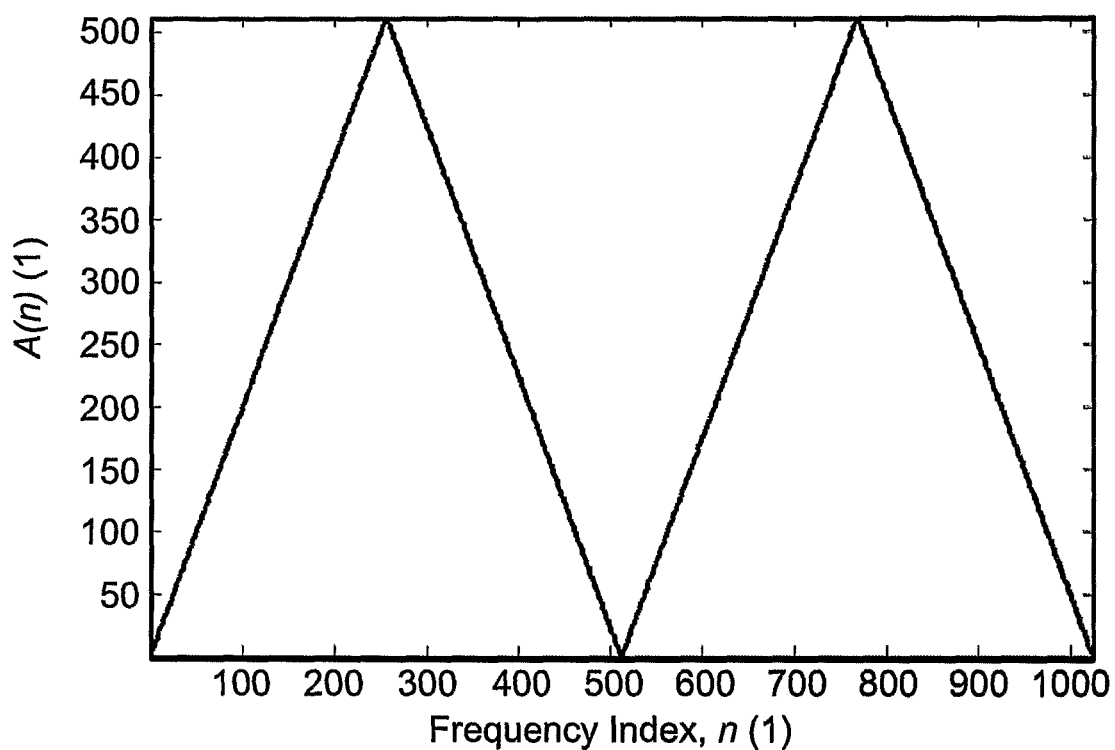
FIG. 3b is a graphical diagram illustrating the number of elements added (or subtracted) during calculation of the actual (signal) Doppler spectrum for each frequency index, A(n), for N=1024, using the Combined method, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

In order to reduce this ratio, one can solve the entire spectrum using both solutions, and combine the results, choosing at each n the method for which A(n) is minimal, as shown in FIG. 3b, being a graphical diagram illustrating the number of elements added (or subtracted) during calculation of the actual (signal) Doppler spectrum for each frequency index, A(n), for N=1024, using the Combined method, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region. The resulting ratio would be approximately $\sqrt{N/2}$. For N=64, the ratio is 5.66.

Furthermore, due to the stochastic nature of the Doppler spectra within the target organs, the signal's autocorrelation time is expected to be relatively short. Consequently, it is theoretically impossible to measure exactly the same Doppler process at two consecutive measurements (using two different PRFs). However, similar effects also occur when the Doppler spectrum is measured using a single PRF: coherent integration is applied to the signal (at the relevant range), as measured at several consecutive pulses, and the short autocorrelation times cause slight smearing of the measured spectra. Since standard PWD imaging produces clinically acceptable analysis, the stochastic phenomena should probably just introduce small inaccuracies to the final estimated frequency spectrum.

According to another main aspect of the present invention, there is provision of a method of using pulsed-wave (PW) ultrasonography for performing an ultrasound or medical imaging procedure on a subject, the method includes the following main steps: (a) transmitting into a region of the subject a plurality of pulse trains of sound waves at two or more different pulse repetition frequencies; (b) spectrally analyzing each pulse train, for evaluating a Doppler frequency spectrum associated with each pulse train; (c) combining frequency components of the Doppler frequency spectrum of each pulse train, for obtaining an aliasing-free instantaneous Doppler frequency spectrum for the region of the subject; and (d) using the Doppler effect for translating the aliasing-free frequency spectrum to the aliasing-free radial velocity spectrum of the matter moving in the region.

The method of using pulsed-wave (PW) ultrasonography for performing an ultrasound or medical imaging procedure on a subject is based on the hereinabove illustrative description, along with reference to FIGS. 1-9, of the exemplary preferred embodiment of the generalized method of using pulsed-wave (PW) ultrasonography for determining an aliasing-free radial velocity spectrum of matter moving in a region.

This includes, for example, the hereinabove illustrative description of the first exemplary specific preferred embodiment of the generalized method being particularly applicable to, and implementable by using, the color flow Doppler (CFD) modality or the tissue Doppler imaging (TDI) modality of pulsed-wave (PW) ultrasonography. This also includes, for example, the hereinabove illustrative description of the second exemplary specific preferred embodiment of the generalized method being particularly applicable to, and implementable by using, the pulsed-wave Doppler (PWD) modality of pulsed-wave (PW) ultrasonography. This also includes, for example, the hereinabove illustrative description of an exemplary preferred embodiment of the method of using pulsed-wave ultrasonography for performing an ultrasound or medical imaging procedure on a subject.

Above illustratively described novel and inventive aspects and characteristics, and advantages thereof, of the present invention further become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

As illustratively described hereinabove, the exemplary preferred embodiment of the generalized method of using pulsed-wave (PW) ultrasonography for determining an aliasing-free radial velocity spectrum of matter moving in a region, is particularly applicable to, and implementable by using, a modality of pulsed-wave ultrasonography selected from the group consisting of color flow Doppler (CFD), tissue Doppler imaging (TDI), and pulsed-wave Doppler (PWD). As illustratively described hereinabove, the first exemplary specific preferred embodiment of the generalized method is particularly applicable to, and implementable by using, the color flow Doppler (CFD) modality or the tissue Doppler imaging (TDI) modality of pulsed-wave (PW) ultrasonography, whereas the second exemplary specific preferred embodiment of the generalized method is particularly applicable to, and implementable by using, the pulsed-wave Doppler (PWD) modality of pulsed-wave (PW) ultrasonography.

Hereinbelow are provided two examples of the hereinabove illustratively described second exemplary specific preferred embodiment of the generalized method, of the present invention, as particularly applicable to, and implementable by using, the pulsed-wave Doppler (PWD) modality of pulsed-wave (PW) ultrasonography. For the examples, algorithms corresponding to the method of the present invention were converted into Matlab computer programs, which were then used for simulating implementation of the present method. The simulations are divided into two groups:

1—Spectrum reconstruction based on noise-free samples.
2—Spectrum reconstruction based on noisy samples.

The computerized simulations illustratively described in Examples 1 and 2 were designed to illustrate implementation of the hereinabove illustratively described method of the present invention.

Example 1

Spectrum Reconstruction Based on Noise-Free Samples

Method

The noise-free simulations use a frequency-limited input signal S(t) of the form expressed by equation (32):

$$S(t) = \sum_{n=0}^{1023} B_n \exp(j \cdot 2\pi n \cdot t) \quad (32)$$

where $B_n$ is the complex amplitude for each frequency, t is the time index, and j is $\sqrt{-1}$ The values of each component of $B_n$ (both real and imaginary) have been randomly selected using a Uniform distribution, in the range [0.0, 1.0].

The simulations use N=1024, and "sample" the signal at $f_{max}$ 1024 Hz, which matches the spectrum of the input signal perfectly, and should therefore produce an Aliasing-free spectrum (note that the power spectrum equals zero at negative frequencies, so we can relate to the frequency range [0, $2f_c$) as describing the entire spectrum). The signal is also sampled and at two lower PRFs: $f_1$=512 Hz, $f_2$=513 Hz. The reconstructed spectrum S″ has been computed based on $f_1$ and $f_2$, using the first method. The magnitude of the error for each component (i.e., the magnitude of the difference between the spectrum measured using $f_{max}$ and the reconstructed spectrum S″) has also been calculated.

Results and Discussion

Figure 4:
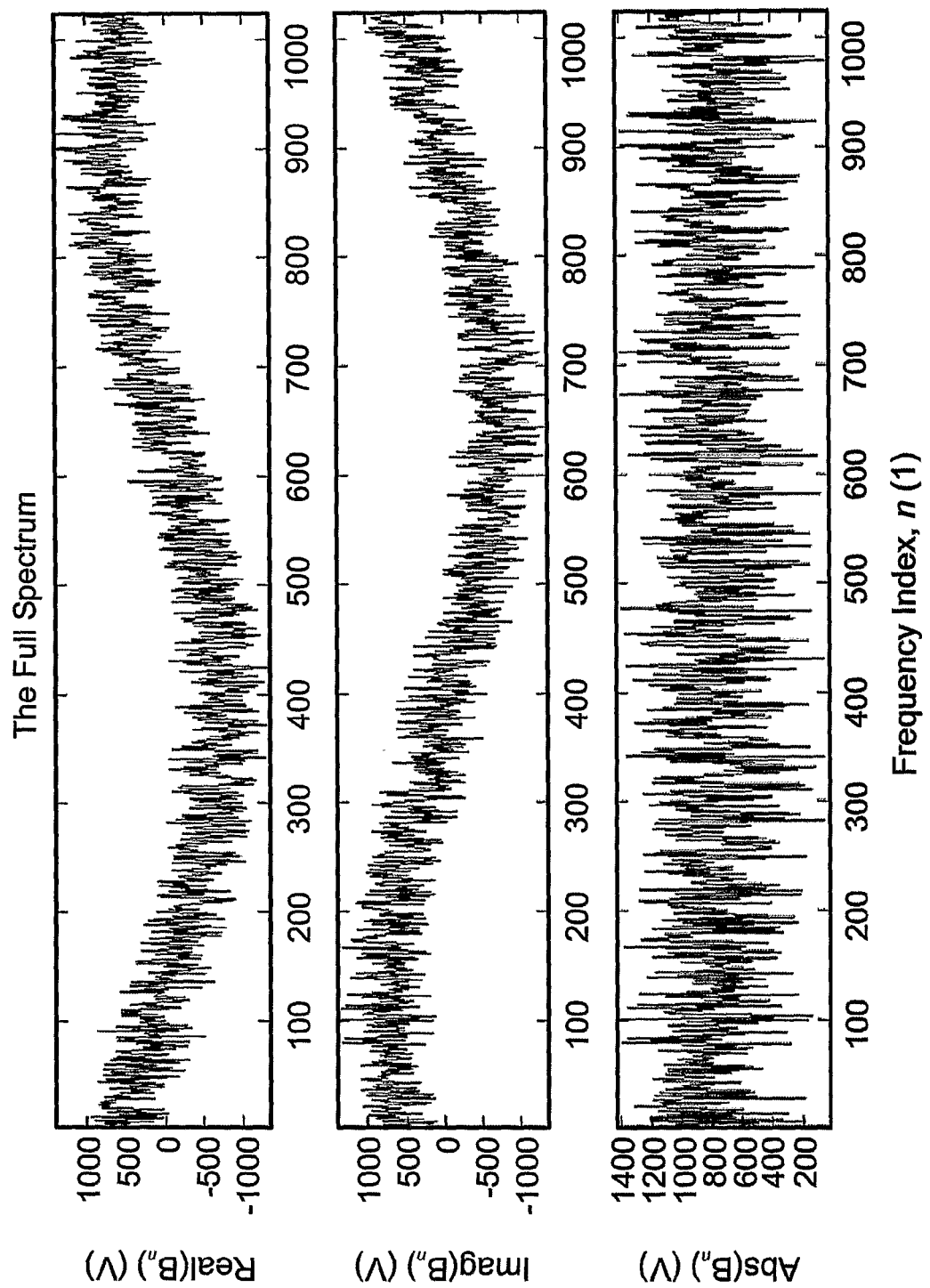
FIG. 4 is a graphical diagram illustrating the actual Doppler spectrum of the input signal S(t), as measured using $f_{max}$, 1024 Hz (i.e., $B_n$), where, the real component of the spectrum is shown in the top graph, the imaginary component is shown in the middle graph, and the magnitude is shown in the bottom graph, as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.
Figure 5A:
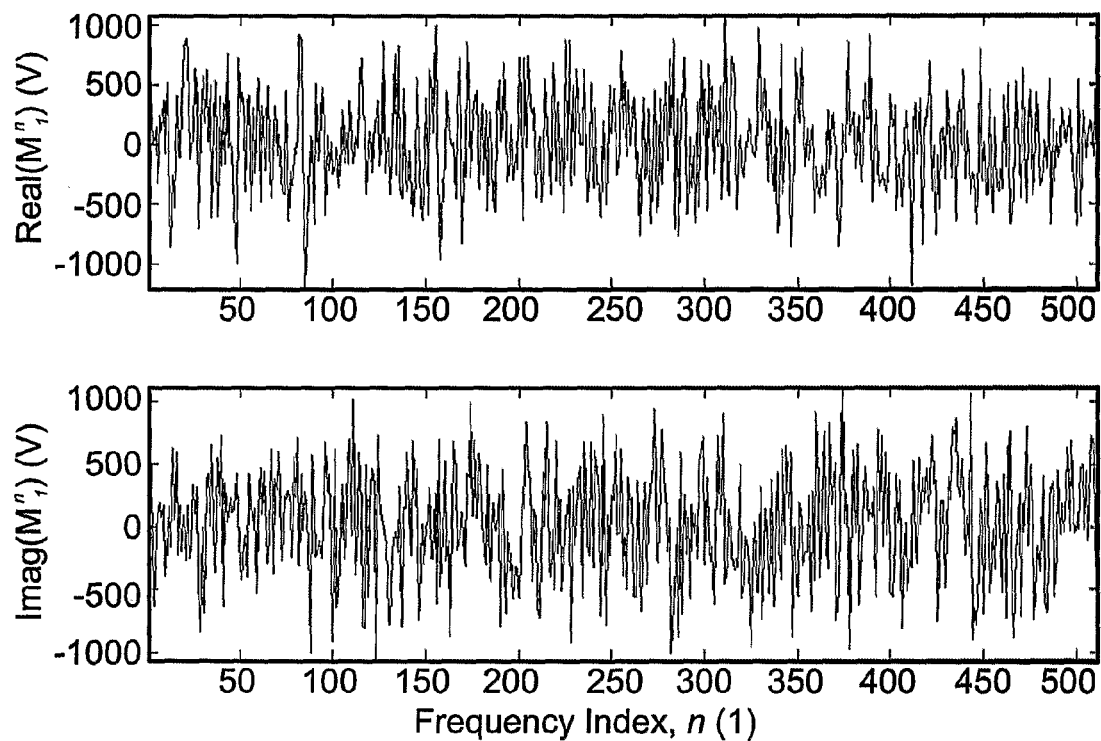
FIGS. 5a and 5b are graphical diagrams illustrating actual Doppler spectra of the input signal S(t), when measured at the first low PRF, $f_1=512$ Hz (i.e., $M_1''$) [FIG. 5a], and at the second low PRF, $f_2=513$ Hz (i.e., $M_2''$) [FIG. 5b], where, in each figure, the real component of the spectrum is shown in the top graph, and the imaginary component is shown in the bottom graph, as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.
Figure 5B:
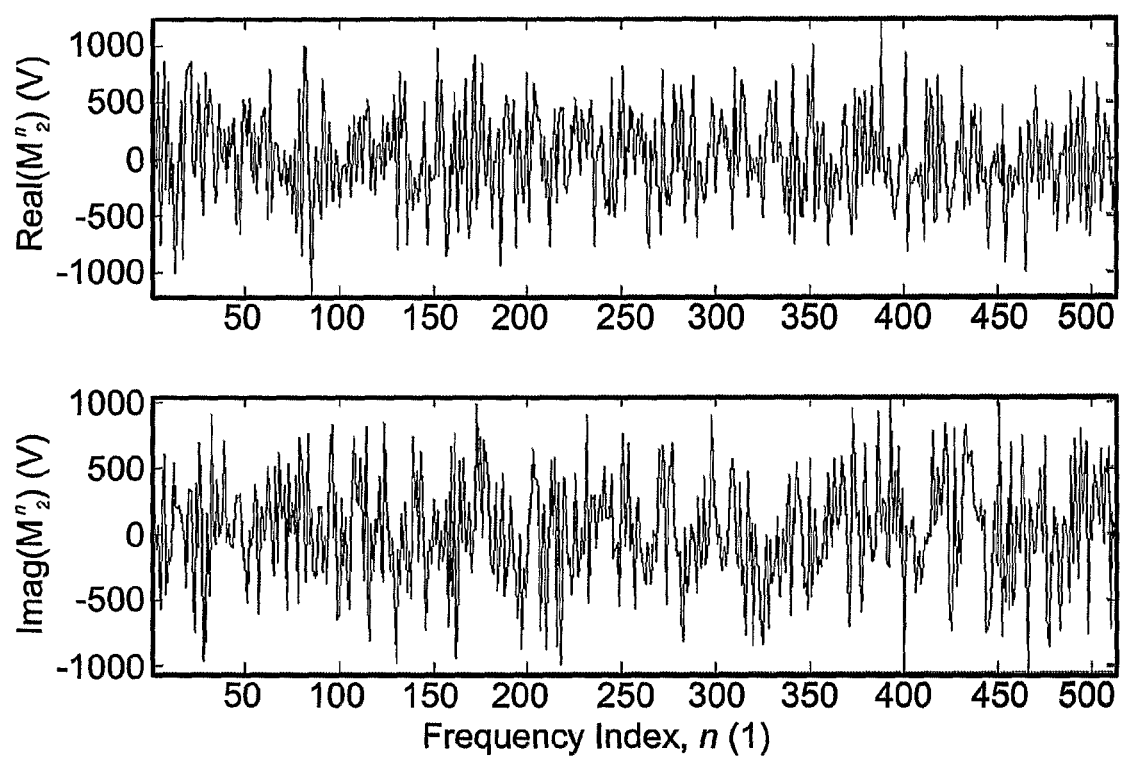

The spectrum of the input signal S(t), sampled at $f_{max}$=1024 Hz, is shown in FIG. 4, being a graphical diagram illustrating the actual Doppler spectrum of the input signal S(t), as measured using $f_{max}$, 1024 Hz (i.e., $B_n$), where, the real component of the spectrum is shown in the top graph, the imaginary component is shown in the middle graph, and the magnitude is shown in the bottom graph, as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region. The spectrum of the signal sampled at the lower PRFs, $f_1$=512 Hz and $f_2$=513 Hz, is shown in FIGS. 5a and 5b, respectively, being graphical diagrams illustrating actual Doppler spectra of the input signal S(t), when measured at the first low PRF, $f_1$=512 Hz (i.e., $M_1$″) [FIG. 5a], and at the second low PRF, $f_2$=513 Hz (i.e., $M_2$″) [FIG. 5b], where, in each figure, the real component of the spectrum is shown in the top graph, and the imaginary component is shown in the bottom graph, as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

Figure 6A:
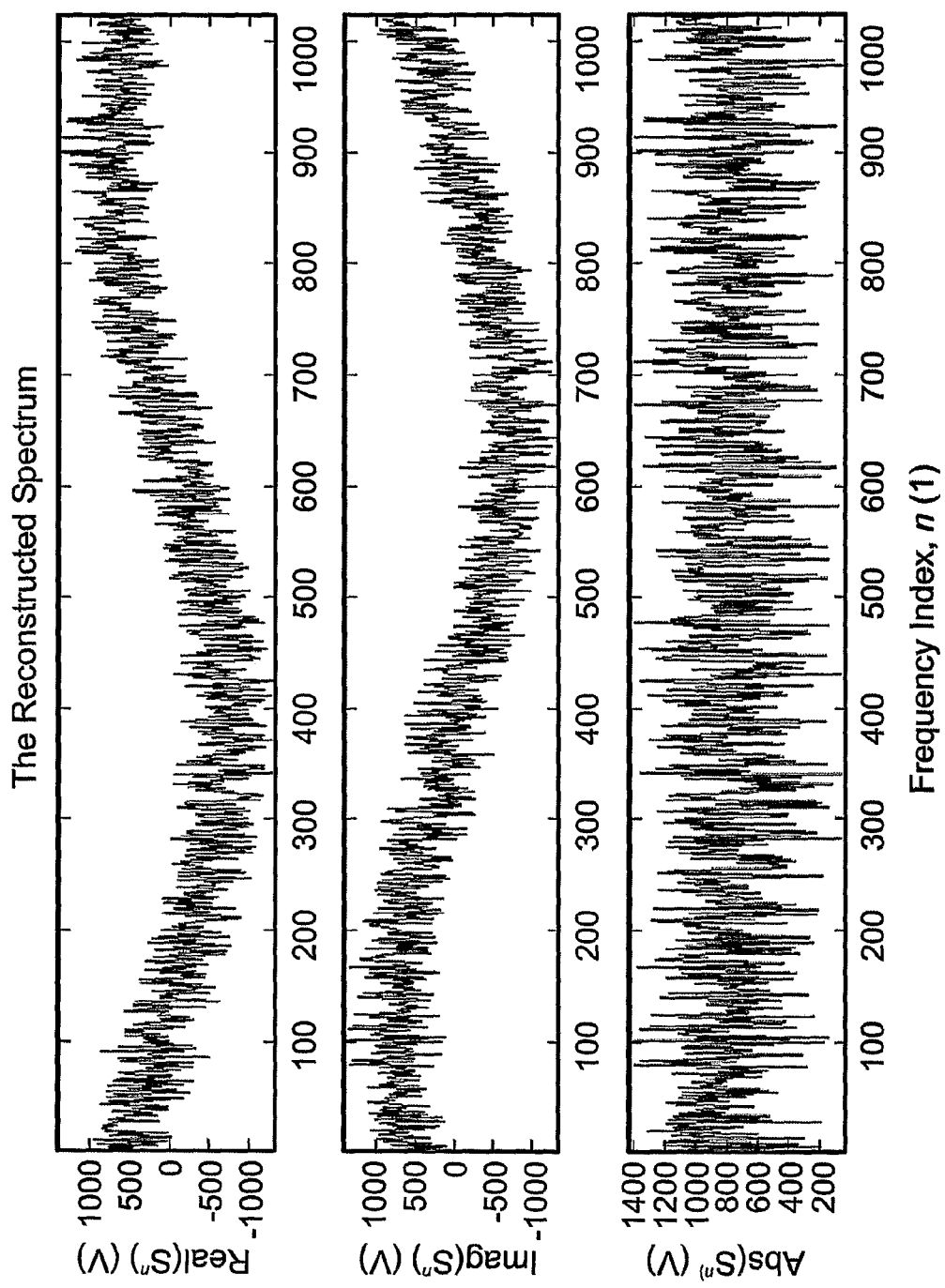
FIG. 6a is a graphical diagram illustrating the reconstructed Doppler spectrum $S''$, based on $f_1$ and $f_2$, where, the real component of the spectrum is shown in the top graph, the imaginary component is shown in the middle graph, and the magnitude is shown in the bottom graph, showing close similarity with the actual (signal) Doppler spectrum, measured using $f_{max}$ (FIGS. 5a and 5b), as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

The reconstructed spectrum S″ is shown in FIG. 6a, being a graphical diagram illustrating the reconstructed Doppler spectrum S″, based on $f_1$ and $f_2$, where, the real component of the spectrum is shown in the top graph, the imaginary component is shown in the middle graph, and the magnitude is shown in the bottom graph, showing close similarity with the actual (signal) Doppler spectrum, measured using $f_{max}$ (FIGS. 5a and 5b), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

Figure 6B:
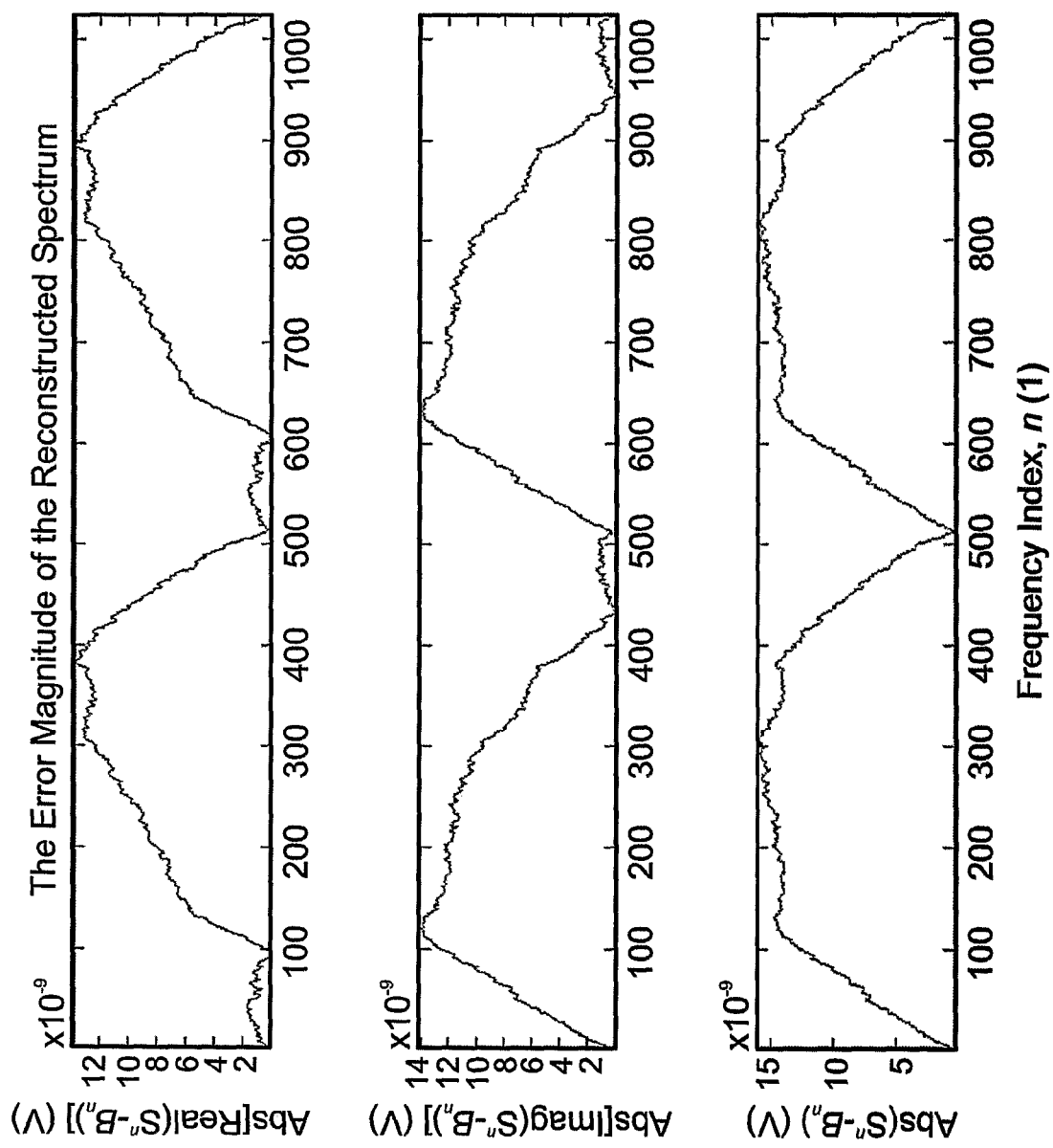
FIG. 6b is a graphical diagram illustrating the error magnitude of each component of the reconstructed Doppler spectrum $S''$ (with respect to $B_n$), where, the real component of the error is shown in the top graph, the imaginary component is shown in the middle graph, and the magnitude is shown in the bottom graph, which show that values of the error are negligible compared to values of the reconstructed Doppler spectrum itself, as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

The error magnitude for each component of S″ (i.e., the magnitude of the difference between the full spectrum $B_n$, measured using $f_{max}$, and the reconstructed spectrum) appears in FIG. 6b, being a graphical diagram illustrating the error magnitude of each component of the reconstructed Doppler spectrum S″ (with respect to $B_n$), where the real component of the error is shown in the top graph, the imaginary component is shown in the middle graph, and the magnitude is shown in the bottom graph, which show that values of the error are negligible compared to values of the reconstructed Doppler spectrum itself, as described in Example 1 (noise-free samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

The reconstructed spectrum S″, seen in FIG. 6a, is clearly very similar to the original spectrum, measured using $f_{max}$ (i.e., the graphs in FIGS. 4 and 6a cannot be visually discerned). This fact is also manifested in the error magnitudes shown in FIG. 6b—the error values are negligible compared to the values of the actual spectrum (there is a difference of almost six orders of magnitude).

Example 2

Spectrum Reconstruction Based on Noisy Samples

Method

The simulations use a single-frequency input signal S(t), of the form expressed by equation (33):

$$S(t) = B\exp(jwt) \quad (33)$$
$$B = 1000 \text{ V}$$
$$\omega = 2\pi \frac{99}{1024} \frac{\text{rad}}{\text{s}}$$

where B is the signal amplitude and w is its radial velocity. The signal has been sampled using N=1024, at the PRFs: $f_1$=512 Hz, $f_2$=513 Hz. When sampling, additive Normally distributed noise has been introduced to each component of the complex sample, with a 0.0 mean and $1/\sqrt{2}$ standard deviation (the magnitude of the noise follows the Rayleigh distribution). The noise-free un-aliased spectrum is denoted $B_n$, whereas the noisy un-aliased spectrum is denoted $N_n$.

For illustration purposes, the complete spectrum S″ has been reconstructed using the first method, followed by computing the error magnitude (i.e., the magnitude of the difference between the reconstructed spectrum and the noise-free spectrum) for each component of each frequency index.

In addition, the abovementioned procedure has been repeated 1000 times, and the histogram of the ratio between the maximal absolute error in the reconstructed spectrum S″ and the mean absolute error in the samples has been plotted for each component. Again, the mean ratio is expected to be $\sqrt{N-1}$, or 31.98 in this example.

Results and Discussion

Figure 7A:
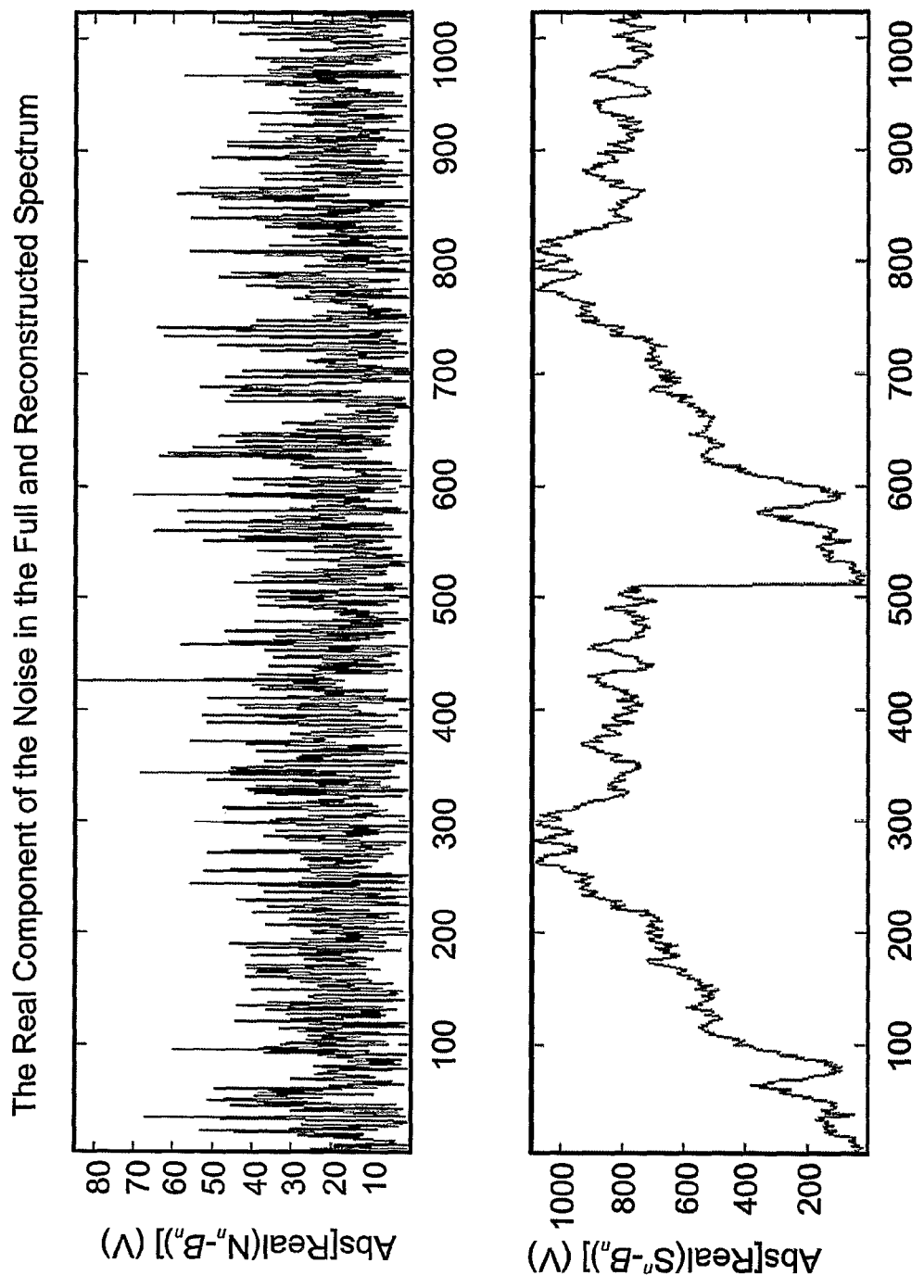
FIG. 7a is a graphical diagram illustrating the components of the noise in both the actual (signal) Doppler spectrum and the reconstructed Doppler spectrum, where the top graph shows the magnitude of the difference between the real component of the noisy spectrum $N_n$, measured using $f_{max}$, and the real component of the noise-free Doppler spectrum $B_n$, also measured using $f_{max}$, and the bottom graph shows the magnitude of the difference between the real component of the reconstructed Doppler spectrum $S''$ and the real component of the noise-free Doppler spectrum $B_n$, measured using $f_{max}$, as described in Example 2 (noisy samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.
Figure 7B:
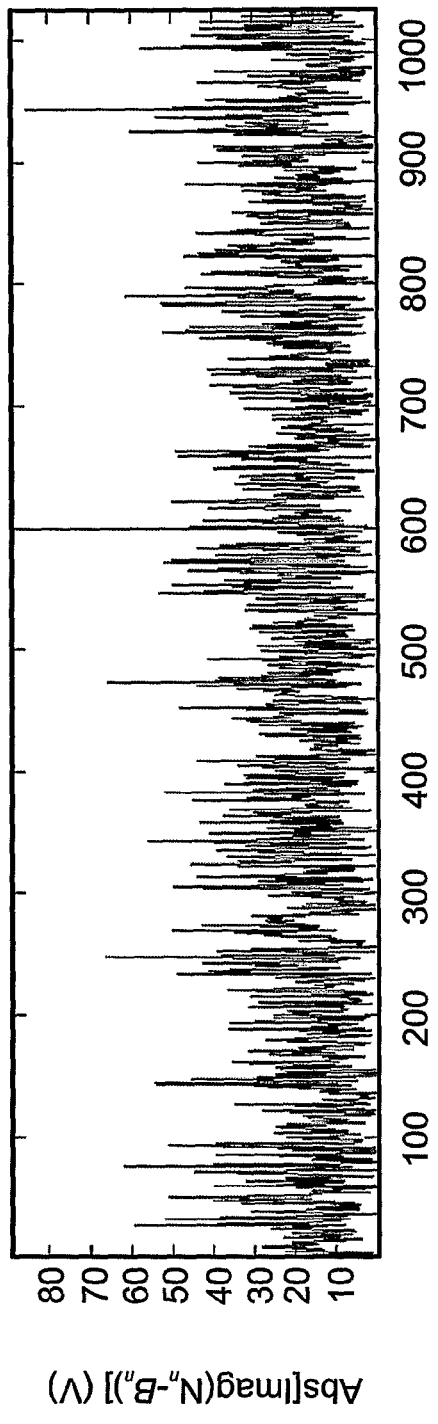
FIG. 7b is a graphical diagram illustrating the magnitude of the difference between the imaginary component of the noisy Doppler spectrum $N_n$, measured using $f_{max}$, and the imaginary component of the noise-free Doppler spectrum $B_n$, also measured using $f_{max}$ [top graph], and the magnitude of the difference between the imaginary component of the reconstructed Doppler spectrum $S''$ and the imaginary component of the noise-free Doppler spectrum $B_n$, measured using $f_{max}$ [bottom graph], as described in Example 2 (noisy samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.
Figure 7B:
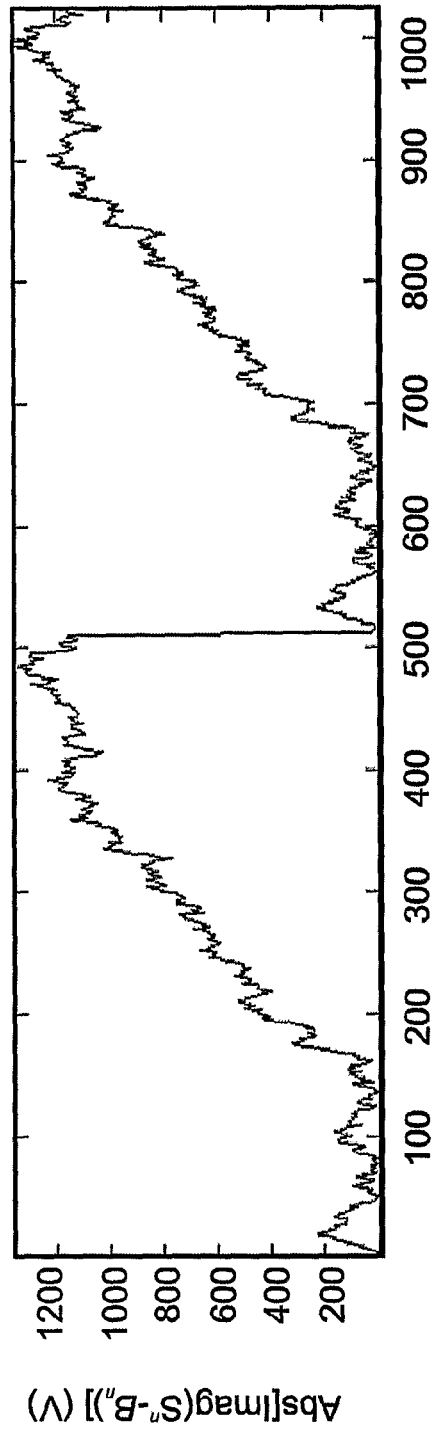
Figure 8:
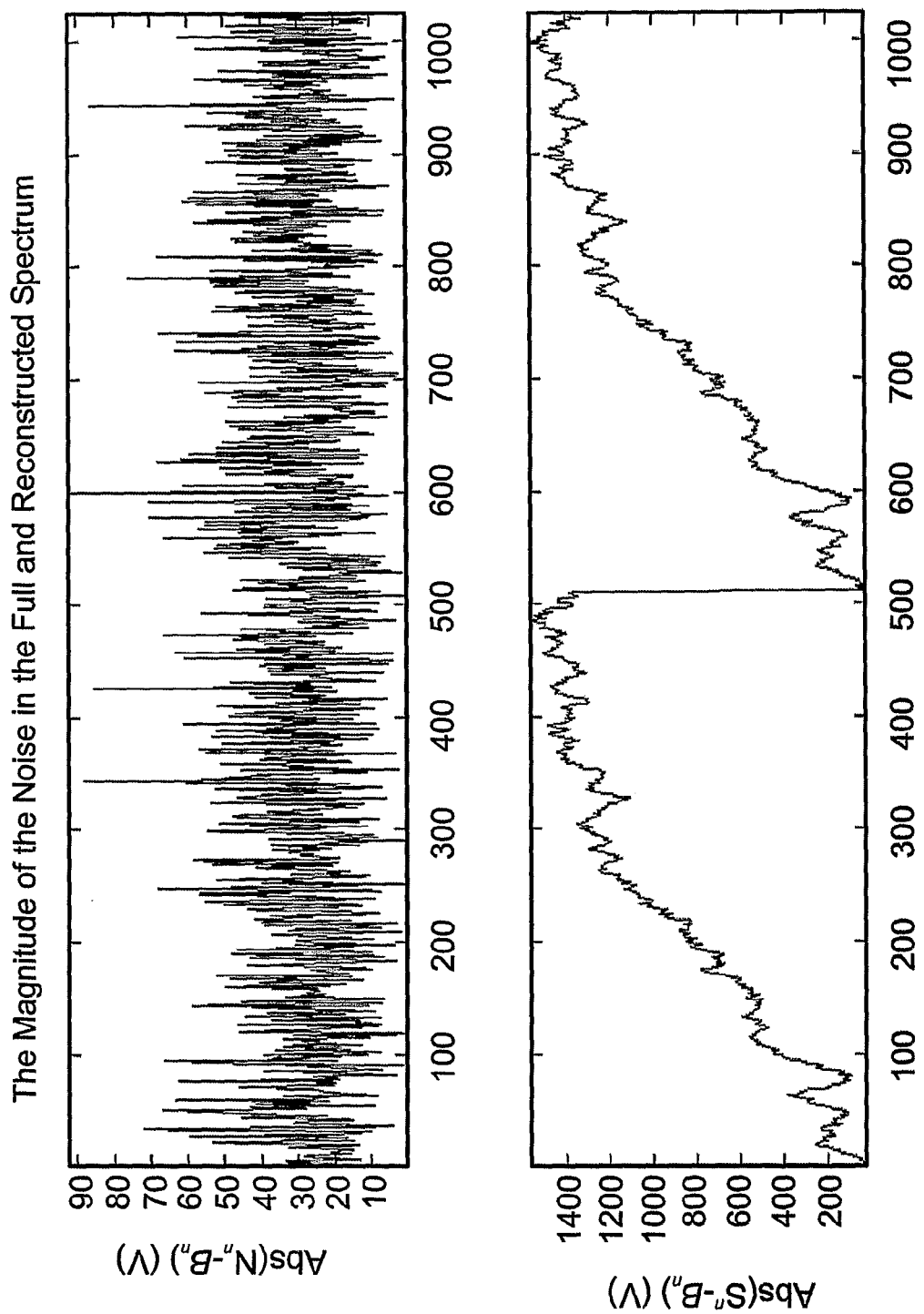
FIG. 8 is a graphical diagram illustrating the magnitude of the noise in both the actual (signal) Doppler spectrum and the reconstructed Doppler spectrum, where, the top graph shows the magnitude of the difference between the noisy spectrum $N_n$, measured using $f_{max}$, and the noise-free Doppler spectrum $B_n$, also measured using $f_{max}$, and the bottom graph shows the magnitude of the difference between the reconstructed Doppler spectrum S″ and the noise-free Doppler spectrum $B_n$, measured using $f_{max}$, as described in Example 2 (noisy samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

FIGS. 7a, 7b, and 8 each include two graphs, describing the noise in both the full (actual) spectrum and the reconstructed spectrum. The magnitude of the difference between a component of the noisy spectrum $N_n$, measured using $f_{max}$, and the corresponding component of the noise-free spectrum $B_n$, also measured using $f_{max}$. The magnitude of the difference between a component of the reconstructed spectrum S″ and the corresponding component of the noise-free spectrum $B_n$, measured using $f_{max}$.

FIG. 7a is a graphical diagram illustrating the components of the noise in both the actual (signal) Doppler spectrum and the reconstructed Doppler spectrum, where the top graph shows the magnitude of the difference between the real component of the noisy spectrum $N_n$, measured using $f_{max}$, and the real component of the noise-free Doppler spectrum $N_n$, also measured using $f_{max}$, and the bottom graph shows the magnitude of the difference between the real component of the reconstructed Doppler spectrum S″ and the real component of the noise-free Doppler spectrum $B_n$, measured using $f_{max}$, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

FIG. 7b is a graphical diagram illustrating the magnitude of the difference between the imaginary component of the noisy Doppler spectrum $N_n$, measured using $f_{max}$, and the imaginary component of the noise-free Doppler spectrum $B_n$, also measured using $f_{max}$ [top graph], and the magnitude of the difference between the imaginary component of the reconstructed Doppler spectrum S″ and the imaginary component of the noise-free Doppler spectrum $B_n$, measured using $f_{max}$ [bottom graph], as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

FIG. 8 is a graphical diagram illustrating the magnitude of the noise in both the actual (signal) Doppler spectrum and the reconstructed Doppler spectrum, where the top graph shows the magnitude of the difference between the noisy spectrum $N_n$, measured using $f_{max}$, and the noise-free Doppler spectrum $B_n$, also measured using $f_{max}$, and the bottom graph shows the magnitude of the difference between the reconstructed Doppler spectrum S″ and the noise-free Doppler spectrum $B_n$, measured using $f_{max}$, as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region.

In all three figures, the bottom graph shows obvious symmetry between the ranges [0, 510] and [513, 1023]. In each range, the shape of the graph closely resembles that of the function $f(x)=\sqrt{x}$, even though the graph is, of course, noisy. This behavior matches the theory—the standard deviation (relating to the error) for each frequency index is proportional to $\sqrt{A(n)}$, where A(n) is described in equation (30).

Figure 9:
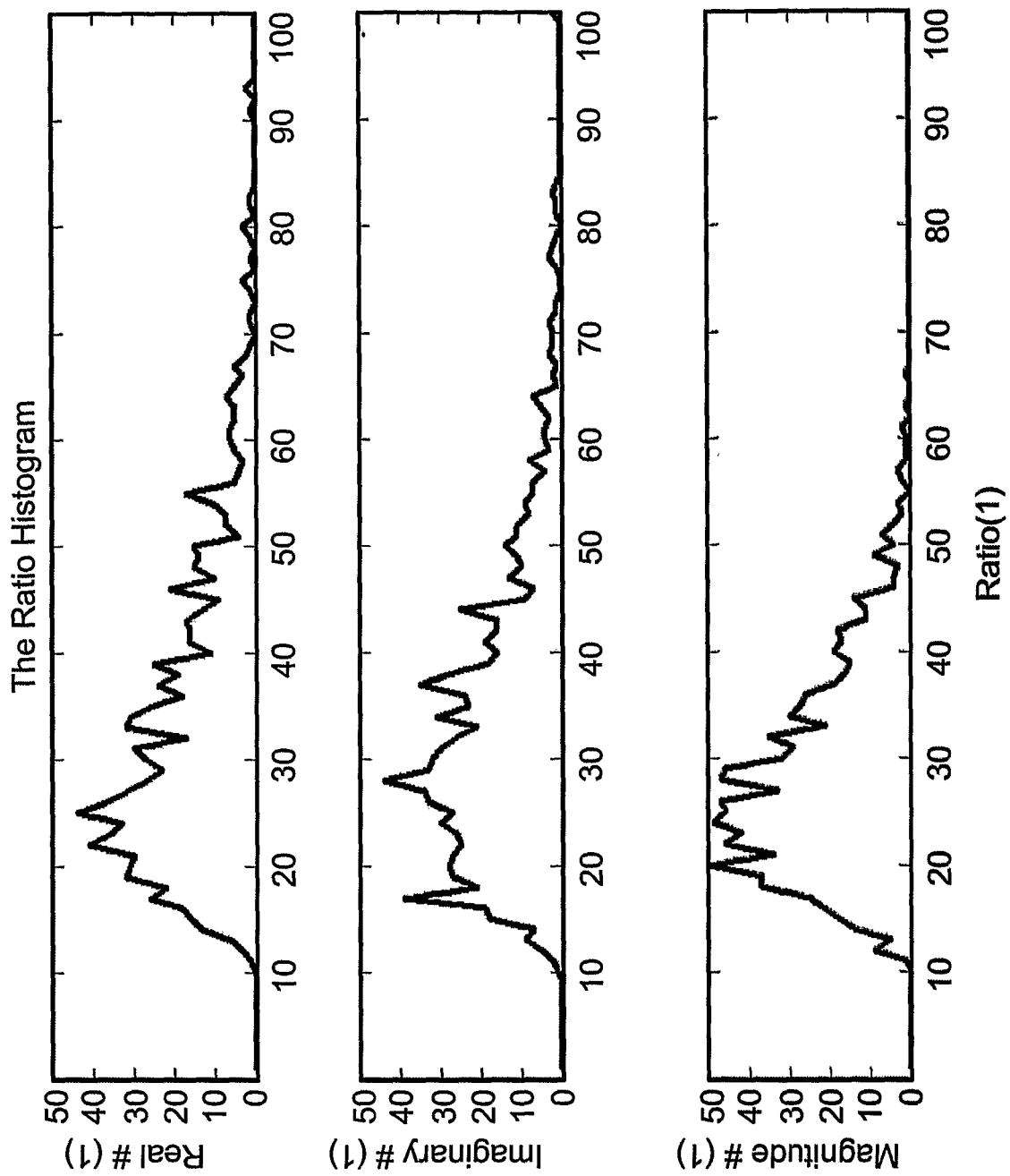
FIG. 9 is a graphical diagram illustrating the histogram of the ratio between the maximal absolute error in the reconstructed Doppler spectrum S″ and the mean absolute error in the samples, based on 1000 trials, where, the top graph shows the real component of the ratio, the middle graph shows the imaginary component the ratio, and the bottom graph shows the magnitude of the ratio, as described in Example 2 (noisy samples), as applied in the pulsed-wave Doppler (PWD) modality of pulsed-wave (PW) ultrasonography, which is used as part of an exemplary specific preferred embodiment of the generalized method for determining an aliasing-free radial velocity spectrum of matter moving in a region, in accordance with the present invention.

FIG. 9 displays the histogram of the ratio between the maximal absolute error in the reconstructed spectrum S'' and the mean absolute error in the samples, based on 1000 trials. The histogram is shown for each component separately, as well as for the magnitude. As explained above, the mean ratio for both the real and the imaginary components is expected to be $\sqrt{N-1}$, or 31.98 in this case. The mean ratio for the real component is 33.54, whereas the mean ratio for the imaginary component is 33.60. The mean ratio for the absolute value is 28.55. The median of the ratios for the real component, the imaginary component and the absolute value are 30.58, 31.04 and 27.08 respectively.

The mean and the median values for both the real or the imaginary components are quite close to the theoretical value of 31.98. This fact provides further corroboration of the hereinabove theoretical analysis. Standard PWD configurations use much lower N values, e.g., 64 or 128. In this simulation, N has been set to 1024 in order to increase the examined effect.

The present invention, as illustratively described and exemplified hereinabove, has several beneficial and advantageous aspects, characteristics, and features, which are based on or/and a consequence of, the above illustratively described main aspects of novelty and inventiveness.

The present invention is implementable by using any of the three main types or modalities, i.e., pulsed-wave Doppler (PWD), color flow Doppler (CFD), or tissue Doppler imaging (TDI), of pulsed-wave (PW) ultrasonography, which are used for measuring and determining radial velocity spectra of matter moving in a region.

The present invention is applicable for determining an aliasing-free radial velocity spectrum of different forms, e.g., liquid or/and solid forms, of matter, moving in a (two-dimensional areal or three-dimensional volumetric) region. Such matter moving in the region is generally any substance or material, composed of organic or/and inorganic species, being of liquid or/and solid form, which is part of a non-living object, or, part of a human or animal subject.

The present invention is implementable in a wide variety of different applications that are practiced in a wide variety of different fields, such as ultrasonography, medical imaging, acoustics, seismology, sonar imaging, radar technology, electronic warfare, lidar (light detection and ranging). An important exemplary application of the present invention in the fields of ultrasonography and medical imaging is echocardiography.

The present invention is commercially applicable by being readily integratable and implementable with currently used pulsed-wave (PW) ultrasonography equipment and hardware (devices, apparatus, systems), such as those manufactured, marketed, or/and sold, by the following well known multi-national companies: General Electric Healthcare, Phillips Medical, Siemens Medical Solutions, Toshiba, and Hitachi.

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

BIBLIOGRAPHY

1. C. A. Walsh and P. Wilde, *Practical Echocardiography*. London: Greenwich Medical Media Limited, 1999, pp. 27-35.
2. P. N. T. Wells, "Ultrasonic colour flow imaging", *Phys Med Biol*, vol. 39, pp. 2113-2145, December, 1994.
3. A. Criton, R. Steel, P. R. Hoskins, W. M. McDicken, and H. F. Routh, "Real time vector Doppler for tissue motion", in *Proc. of* 2002 *IEEE International Ultrasonics Symposium*, 2002, vol. 2, pp. 1529-1534.
4. W. H. Press, S. A. Teukolsky, W. T. Vetterling, and B. P. Flannery, *Numerical Recipes in C: The Art of Scientific Computing*. Cambridge: Cambridge University Press, 1997, pp. 496-536.
5. A. Lange, P. Palka, P. Caso, L. N. Fenn, R. Olszewski, M. P. Ramo, T. R. D. Shaw, A. Nowicki, K. A. A. Fox, and G. R. Sutherland, "Doppler myocardial imaging vs. B-Mode gray-scale imaging: A comparative in-vitro and in-vivo study into their relative efficacy in endocardial boundary detection", *Ultrasound Med Biol*, vol. 23, pp. 69-75, January 1997.
6. K. R. Baek, M. H. Bae, and S. B. Park, "A new aliasing extension method for ultrasonic 2-dimensional pulsed Doppler systems", *Ultrasonic Imaging*, vol. 11, pp. 233-244, October, 1989.
7. C. J. Hartley, "Resolution of frequency aliases in ultrasonic pulsed Doppler velocimeters", *IEEE Trans. Sonics Ultrason.*, vol. 28, pp. 69-75, March, 1981.
8. A. P. G. Hoeks, H. P. M. Peeters, C. J. Ruissen, and R. S. Reneman, "A novel frequency estimator for sampled Doppler signals", *IEEE Trans. Biomed. Eng.*, vol. 31, pp. 212-220, February, 1984.
9. P. Tortoli, F. Valgimigli, G. Guidi, and P. Pignoli, "Clinical evaluation of a new anti-aliasing technique for ultrasound pulsed Doppler analysis", *Ultrasound Med Biol*, vol. 15, pp. 749-756, August, 1989.
10. H. Torp, and K. Kristoffersen, "Velocity matched spectrum analysis: a new method for suppressing velocity ambiguity in pulsed-wave Doppler", *Ultrasound Med Biol*, vol. 21, pp. 937-944, July, 1995.
11. V. L. Newhouse, P. LeCong, E. S. Furgason, and C. T. Ho, "On increasing the range of pulsed Doppler systems for blood flow measurement", *Ultrasound Med Biol*, vol. 6, pp. 233-237, March, 1980.
12. H. J. Nitzpon, J. C. Rajaonah, C. B. Burckhardt, B. Dousse, and J. J. Meister, "A new pulsed wave Doppler ultrasound system to measure blood velocities beyond the Nyquist limit", *IEEE Trans. Ultrason., Ferroelect., Freq. Contr.*, vol. 42, pp. 265-279, March, 1995.
13. M. I. Skolnik, *Radar Handbook*. Boston, Mass.: McGraw-Hill Inc., 1990, Ch. 17.

What is claimed is:

1. A method of using pulsed-wave ultrasonography for determining an aliasing-free radial velocity spectrum of matter moving in a region, the method comprising:
   (a) transmitting into the region a plurality of pulse trains of sound waves at two or more different pulse repetition frequencies;
   (b) spectrally analyzing each said pulse train, for evaluating a Doppler frequency spectrum associated with each said pulse train;
   (c) combining frequency components of said Doppler frequency spectrum of each said pulse train, for obtaining an aliasing-free instantaneous Doppler frequency spectrum for the region, and solving a series of recursive equations, wherein each said recursive equation describes dependence of said frequency components of said Doppler frequency spectrum of each said pulse train on said aliasing-free instantaneous Doppler frequency spectrum for the region;
   (d) using Doppler effect for translating said aliasing-free Doppler frequency spectrum to the aliasing-free radial velocity spectrum of the matter moving in the region, and
   an initial condition for solving said series of recursive equations is where maximal non-zero Doppler frequency component of said aliasing-free instantaneous Doppler frequency spectrum is known a priori, or
   an analog low-pass filter is applied to signals returned for each said pulse train, and an initial condition for solving said series of recursive equations is where maximal non-zero Doppler frequency component of said aliasing-free instantaneous Doppler frequency spectrum is a pre-determined constant matching a transfer function of said low-pass filter.

2. The method of claim 1, wherein step (a), said plurality of pulse trains of sound waves are alternately or simultaneously transmitted into the region at said two or more different pulse repetition frequencies.

3. The method of claim 2, wherein said simultaneous transmission involves use of a different phase coding or/and a different carrier frequency of said sound waves, for each said pulse repetition frequency.

4. The method of claim 1, wherein step (b) includes applying at least one spectral analysis technique selected from the group consisting of Discrete Fourier Transform (DFT), Fast Fourier Transform (FFT), signal correlation, Burg method, and Minimum Variance Method (MVM).

5. The method of claim 1, wherein step (c) includes imposing a specific assumption regarding said aliasing-free instantaneous Doppler frequency spectrum for the region.

6. The method of claim 1, wherein the pulsed-wave ultrasonography is of a pulsed-wave Doppler (PWD) modality.

7. The method of claim 1, wherein said pulse repetition frequencies and a number of pulses in each said pulse train are determined, for obtaining a same frequency resolution of each said Doppler frequency spectrum associated with each said pulse train.

8. The method of claim 1, wherein the matter is blood or tissue.

9. The method of claim 8, wherein said blood or tissue is moving in an organ in a body of a human or animal subject.

10. The method of claim 1, wherein the matter is lava, ground water, or petroleum.

11. The method of claim 1, wherein the matter is a vehicle, a marine craft, an aircraft, or a space craft.

12. The method of claim 1, wherein the matter is a ground based small sized landscape object or feature.

13. The method of claim 1, wherein the region is segment of a surface, or a segment of a two-dimensional or three-dimensional space.

14. The method of claim 1, wherein the region is part of a wet or dry environment.

15. The method of claim 1, used in a type of procedure selected from the group consisting of ultrasonography, medical imaging, acoustics, seismology, sonar imaging, radar technology, electronic warfare, and lidar (light detection and ranging).

16. A method of using pulsed-wave ultrasonography for performing an ultrasound or medical imaging procedure on a subject, the method comprising:
   (a) transmitting into a region of the subject a plurality of pulse trains of sound waves at two or more different pulse repetition frequencies;
   (b) spectrally analyzing each said pulse train, for evaluating a Doppler frequency spectrum associated with each said pulse train;
   (c) combining frequency components of said Doppler frequency spectrum of each said pulse train, for obtaining an aliasing-free instantaneous Doppler frequency spectrum for a region of the subject, and solving a series of recursive equations, wherein each said recursive equation describes dependence of said frequency components of said Doppler frequency spectrum of each said pulse train on said aliasing-free instantaneous Doppler frequency spectrum for the region;
   (d) using Doppler effect for translating said aliasing-free Doppler frequency spectrum to an aliasing-free radial velocity spectrum of matter moving in said region, and
   an initial condition for solving said series of recursive equations is where maximal non-zero Doppler frequency component of said aliasing-free instantaneous Doppler frequency spectrum is known a priori, or
   an analog low-pass filter is applied to signals returned for each said pulse train, and an initial condition for solving said series of recursive equations is where maximal non-zero Doppler frequency component of said aliasing-free instantaneous Doppler frequency spectrum is a pre-determined constant matching a transfer function of said low-pass filter.

17. The method of claim 16, wherein step (a), said plurality of pulse trains of sound waves are alternately or simultaneously transmitted into said region at said two or more different pulse repetition frequencies.

18. The method of claim 17, wherein said simultaneous transmission involves use of a different phase coding or/and a different carrier frequency of said sound waves, for each said pulse repetition frequency.

19. The method of claim 16, wherein step (b) includes applying at least one spectral analysis technique selected from the group consisting of Discrete Fourier Transform (DFT), Fast Fourier Transform (FFT), signal correlation, Burg method, and Minimum Variance Method (MVM).

20. The method of claim 16, wherein step (c) includes imposing a specific assumption regarding said aliasing-free instantaneous Doppler frequency spectrum for said region.

21. The method of claim 16, wherein the pulsed-wave ultrasonography is of a pulsed-wave Doppler (PWD) modality.

22. The method of claim 16, wherein said pulse repetition frequencies and a number of pulses in each said pulse train are determined, for obtaining a same frequency resolution of each said Doppler frequency spectrum associated with each said pulse train.

23. The method of claim 16, wherein the matter is blood or tissue.

24. The method of claim 23, wherein said blood or tissue is moving in an organ in a body of a human or animal subject.

25. The method of claim 16, wherein said region is segment of a surface, or a segment of a two-dimensional or three-dimensional space.

26. The method of claim 16, wherein the region is part of a wet or dry environment.

* * * * *